United States Patent
Androsov et al.

(10) Patent No.: US 10,071,949 B2
(45) Date of Patent: Sep. 11, 2018

(54) POLYMERIZABLE LIQUID CRYSTAL COMPOUND, COMPOSITION FOR OPTICAL FILM, AND OPTICAL FILM, COMPENSATION FILM, ANTIREFLECTIVE FILM, AND DISPLAY DEVICE INCLUDING THE SAME

(71) Applicant: SAMSUNG ELECTRONICS CO., LTD., Suwon-si, Gyeonggi-do (KR)

(72) Inventors: Dmitry Androsov, Suwon-si (KR); Joungeun Yoo, Seongnam-si (KR); Ju Hyun Kim, Anyang-si (KR); Eun Sung Lee, Hwaseong-si (KR); Changki Kim, Suwon-si (KR); Hyunseok Choi, Anyang-si (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 3 days.

(21) Appl. No.: 15/392,507

(22) Filed: Dec. 28, 2016

(65) Prior Publication Data
US 2017/0183286 A1    Jun. 29, 2017

(30) Foreign Application Priority Data
Dec. 29, 2015 (KR) ......................... 10-2015-0188898

(51) Int. Cl.
| | | |
|---|---|---|
| *G02F 1/1333* | (2006.01) | |
| *C07C 65/21* | (2006.01) | |
| *C07C 235/64* | (2006.01) | |
| *C08F 122/20* | (2006.01) | |
| *C09D 135/02* | (2006.01) | |
| *C09K 19/38* | (2006.01) | |
| *G02B 5/30* | (2006.01) | |
| *C09K 19/18* | (2006.01) | |
| *C09K 19/20* | (2006.01) | |
| *C09K 19/04* | (2006.01) | |

(52) U.S. Cl.
CPC ............ *C07C 65/21* (2013.01); *C07C 235/64* (2013.01); *C08F 122/20* (2013.01); *C09D 135/02* (2013.01); *C09K 19/18* (2013.01); *C09K 19/2014* (2013.01); *C09K 19/3838* (2013.01); *G02B 5/3016* (2013.01); *C09K 2019/0448* (2013.01); *C09K 2219/03* (2013.01)

(58) Field of Classification Search
CPC ............... C09K 19/3838; C09K 19/18; C09K 19/2014; C09K 2019/0448; C09K 2019/03; G02F 1/1333; C07C 65/21; C07C 235/64; C08F 122/20; C09D 135/02; G02B 5/3016
USPC ....................... 252/299.01; 428/1.1
See application file for complete search history.

(56) References Cited

U.S. PATENT DOCUMENTS

| 6,139,771 A | 10/2000 | Walba et al. | |
|---|---|---|---|
| 7,169,325 B2 * | 1/2007 | Nishikawa | C09K 19/18 |
| | | | 252/299.01 |
| 7,667,801 B2 | 2/2010 | Fukagawa et al. | |
| 8,293,146 B2 | 10/2012 | Uehira et al. | |
| 8,557,142 B2 | 10/2013 | Montenegro et al. | |
| 2005/0012071 A1 | 1/2005 | Nishikawa et al. | |
| 2005/0133760 A1 | 6/2005 | Farrand et al. | |
| 2006/0083867 A1 | 4/2006 | Ito et al. | |
| 2011/0147657 A1 | 6/2011 | Hirai et al. | |
| 2015/0369982 A1 | 12/2015 | Sargent | |

FOREIGN PATENT DOCUMENTS

| DE | 247227 A1 | 3/1986 |
|---|---|---|
| EP | 2728388 A1 | 5/2014 |
| GB | 2188048 A | 2/1987 |
| JP | 3325560 B2 | 7/2002 |
| JP | 2003-057441 A | 2/2003 |
| JP | 2007-086748 A | 4/2007 |
| JP | 2010-522892 A | 7/2010 |
| KR | 2006-0090172 A | 8/2006 |
| KR | 2012-0100943 A | 9/2012 |

OTHER PUBLICATIONS

Daisuke Yokoyama et al. "In situ real-time spectroscopic ellipsometry measurement for the investigation of molecular orientation in organic amorphous multilayer structures", Journal of Applied Physics 107 (2010) 123512.
Jorg Frischeisen et al. "Increased light outcoupling efficiency in dye-doped small molecule organic light-emitting diodes with horizontally oriented emitters", Organic Electronics 12 (2011) 809-817.
W. Weissflog et al. "Liquid-crystalline compounds with lateral aromatic branches", Liquid Crystals, 1988, 3(2), 275-284.
Chizu Sekine et al. "High birefringence photopolymerizable phenylacetylene liquid crystals", Liquid Crystals, 2001, vol. 28, No. 10, 1505-1512.
Extended European Search Report dated May 9, 2017, issued for the corresponding European Patent Application No. 16207121.1-1375.
Yuki Arakawa et al. "Highly birefringent polymer films from the photo-crosslinking polymerisation of bistolane-based methacrylate monomers", Liquid Crystals, 2015, vol. 42, No. 10, 1419-1427.

* cited by examiner

*Primary Examiner* — Geraldina Visconti
(74) *Attorney, Agent, or Firm* — Cantor Colburn LLP

(57) ABSTRACT

A polymerizable liquid crystal compound represented by Chemical Formula 1:

Chemical Formula 1

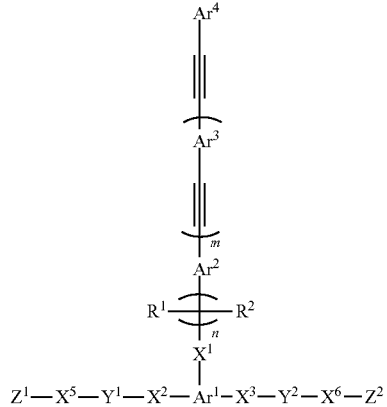

wherein in Chemical Formula 1, groups and variables are the same as defined in the detailed description.

26 Claims, 11 Drawing Sheets

POLYMERIZABLE LIQUID CRYSTAL COMPOUND, COMPOSITION FOR OPTICAL FILM, AND OPTICAL FILM, COMPENSATION FILM, ANTIREFLECTIVE FILM, AND DISPLAY DEVICE INCLUDING THE SAME

CROSS-REFERENCE TO RELATED APPLICATION

This application claims priority to Korean Patent Application No. 10-2015-0188898, filed in the Korean Intellectual Property Office on Dec. 29, 2015, and all the benefits accruing therefrom under 35 U.S.C. § 119, the content of which is incorporated herein in its entirety by reference.

BACKGROUND

1. Field

This disclosure relates to a polymerizable liquid crystal compound, a composition for an optical film, and an optical film, a compensation film, an antireflective film, and a display device including the same.

2. Description of the Related Art

A display device such as a liquid crystal display (LCD) and an organic light emitting diode (OLED) includes a polarizing film attached to the outside of a display panel. The polarizing film only transmits light of a specific wavelength and absorbs or reflects other light, thus controlling the direction of incident light on the display panel or light emitted from the display panel.

The polarizing film generally includes a polarizer and a protective layer for the polarizer. The polarizer may include, for example, iodine or a dichroic dye adsorbed and arranged in polyvinyl alcohol (PVA), and the protective layer may include, for example, triacetyl cellulose (TAC).

The polarizing film is bonded with an optical compensation film, and thus may function as an antireflective film by preventing reflection of external light. The antireflective film may be disposed on one surface or both surfaces of a display device, and thus may influence visibility of the display device.

The optical compensation film including a liquid crystal compound has recently been used for optical compensation and enlargement of a viewing angle of a liquid crystal display (LCD). Since this liquid crystal compound needs to be dissolved in an organic solvent and coated to form an optical compensation film, the liquid crystal compound requires excellent solubility in an organic solvent and excellent miscibility. In addition, it is required that the liquid crystal compound have a region of maintaining a wide enantiotropic nematic phase as well as excellent structural stability and a low melting point.

Thus, there remains a need in a new liquid crystal compound having improved properties.

SUMMARY

An embodiment provides a polymerizable liquid crystal compound capable of improving coating properties and film workability due to improved solubility in organic solvent and having miscibility, stability of a liquid crystal phase, a wide nematic phase region, and a low melting point.

Another embodiment provides a composition for an optical film including the polymerizable liquid crystal compound.

Yet another embodiment provides an optical film including the polymerizable liquid crystal compound or the composition for an optical film.

Still another embodiment provides a compensation film including the optical film and a retardation film disposed on at least one surface of the optical film.

Further embodiment provides an antireflective film including the optical film.

Further embodiment provides a display device including the optical film or the antireflective film.

According to an embodiment, a polymerizable liquid crystal compound is represented by Chemical Formula 1.

Chemical Formula 1

$$Z^1-X^5-Y^1-X^2-Ar^1-X^3-Y^2-X^6-Z^2$$

with substituents $Ar^4$, $Ar^3$ (repeated $m$ times), $Ar^2$, and $R^1$, $R^2$ (repeated $n$ times) and $X^1$ attached to $Ar^1$.

In Chemical Formula 1

$Ar^1$ is a substituted or unsubstituted trivalent aromatic hydrocarbon group, $Ar^2$ and $Ar^3$ are independently a substituted or unsubstituted divalent aromatic hydrocarbon group, $Ar^4$ is a substituted or unsubstituted monovalent aromatic hydrocarbon group, $X^1$ is selected from —C(=O)O— and —C(=O)N($R^a$)— (wherein $R^a$ is hydrogen, a C1 to C20 alkyl group, or a C6 to C30 aryl group), $R^1$ and $R^2$ are independently selected from hydrogen, a halogen, a cyano group, a nitro group, an aldehyde group, a C2 to C30 ketone group, a C2 to C30 ester group, a C1 to C30 alkylsulfonyl group, and a substituted or unsubstituted C1 to C20 alkyl group, n is an integer of 0 to 2, m is 1 or 2, $X^2$ and $X^3$ are independently selected from —OC(=O)—, —C(=O)O—, —N($R^a$)C(=O)—, and —C(=O)N($R^a$)— (wherein $R^a$ is hydrogen, a C1 to C20 alkyl group, or a C6 to C30 aryl group), $Y^1$ and $Y^2$ are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof, $X^5$ and $X^6$ are independently a linking group selected from —OC(=O)—, —C(=O)O—, —S—, —O—, —S(=O)—, —C(=O)—, —S(=O)$_2$—, —N($R^a$)—, —C(=O)S—, —N($R^b$)C(=O)—, and —C(=O)N($R^c$)— (wherein $R^a$, $R^b$, and $R^c$ are independently selected from hydrogen, a C1 to C20 alkyl group, and a C6 to C30 aryl group), or a C2 to C20 alkylene group, wherein at least one —(CH$_2$)— group is replaced by the above linking group in the main chain, and $Z^1$ and $Z^2$ are independently a C2 to C30 polymerizable functional group.

The polymerizable liquid crystal compound represented by Chemical Formula 1 may be represented by Chemical Formula 2.

Chemical Formula 2

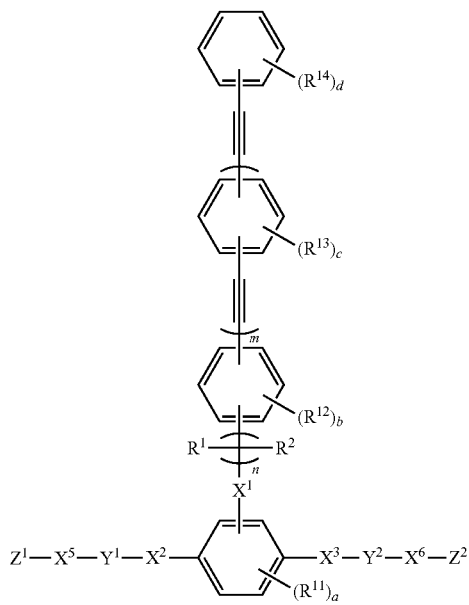

In Chemical Formula 2, $X^1$ is selected from —C(=O)O— and —C(=O)N(R$^a$)— (wherein R$^a$ is hydrogen, a C1 to C20 alkyl group, or a C6 to C30 aryl group), $R^1$ and $R^2$ are independently selected from hydrogen, a halogen, a cyano group, a nitro group, an aldehyde group, a C2 to C30 ketone group, a C2 to C30 ester group, a C1 to C30 alkylsulfonyl group, and a substituted or unsubstituted C1 to C20 alkyl group, n is an integer of 0 to 2, m is 1 or 2, $R^{11}$, $R^{12}$, $R^{13}$, and $R^{14}$ are independently selected from hydrogen, a halogen, a cyano group, a nitro group, an aldehyde group, and a substituted or unsubstituted C1 to C20 alkyl group, a, b, c, and d are independently determined according to the valence of phenylene, $X^2$ and $X^3$ are independently selected from —OC(=O)—, —C(=O)O—, —N(R$^a$)C(=O)—, and —C(=O)N(R$^a$)— (wherein R$^a$ is hydrogen, a C1 to C20 alkyl group, or a C6 to C30 aryl group), $Y^1$ and $Y^2$ are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof, $X^5$ and $X^6$ are independently a linking group selected from —OC(=O)—, —C(=O)O—, —S—, —O—, —S(=O)—, —C(=O)—, —S(=O)$_2$—, —N(R$^a$)—, —C(=O)S—, —N(R$^b$)C(=O)—, and —C(=O)N(R$^c$)—

(wherein R$^a$, R$^b$, and R$^c$ are independently selected from hydrogen, a C1 to C20 alkyl group, and a C6 to C30 aryl group), or a C2 to C20 alkylene group, wherein at least one —(CH$_2$)— group is replaced by the above linking group in the main chain, and $Z^1$ and $Z^2$ are independently a C2 to C30 polymerizable functional group.

The Ar$^1$ may be an aromatic hydrocarbon group represented by Chemical Formula 1-1.

Chemical Formula 1-1

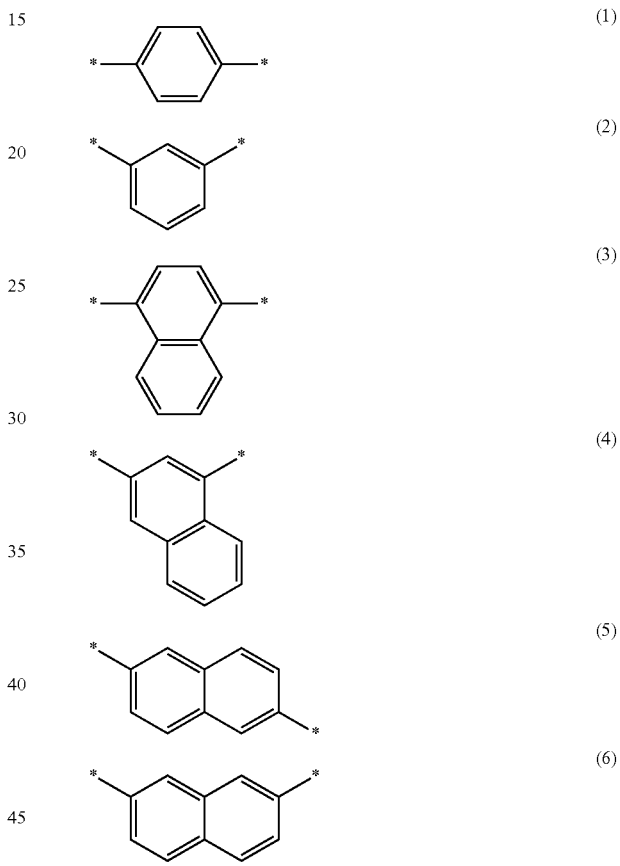

In Chemical Formula 1-1, a hydrogen bound to each aromatic ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)R$^a$), a substituted or unsubstituted C2 to C20 ester group (—C(=O)OR$^b$), a substituted or unsubstituted C3 to C30 cycloalkyl group, a substituted or unsubstituted C6 to C30 aryl group, —S(=O)R$^c$, —S(=O)OR$^d$, —S(=O)$_2$R$^e$, or —S(=O)$_2$OR$^f$ (wherein R$^a$ to R$^f$ are selected from hydrogen, a C1 to C20 alkyl group, and a C6 to C30 aryl group), at least one =CH— group of each aromatic ring is optionally replaced by =N—, and two asterisks indicates linking points bound to $X^2$ and $X^3$.

In Chemical Formula 1 or 2, examples of —C(R¹)(R²)— may be a functional group represented by Chemical Formula 1-2:

Chemical Formula 1-2

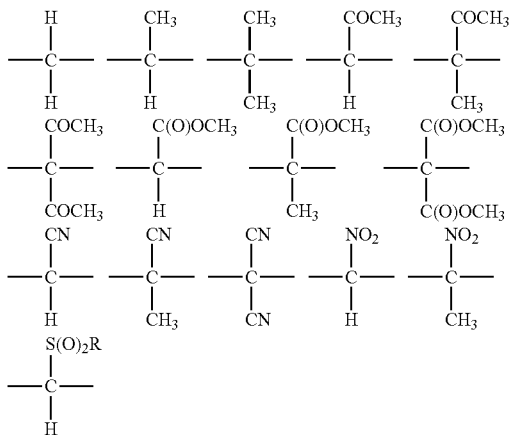

In Chemical Formula 1-2,
R is selected from a C1 to C20 alkyl group and a C6 to C30 aryl group.

The Y¹ and Y² may independently be a functional group represented by Chemical Formula 1-3:

Chemical Formula 1-3

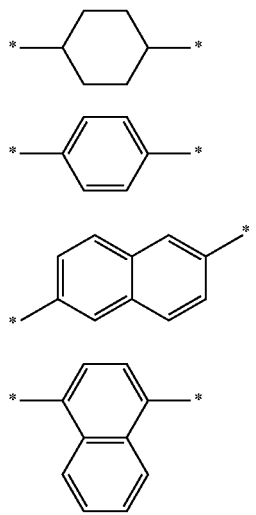

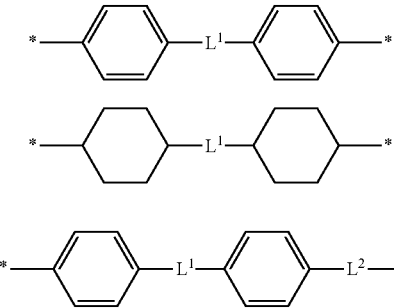

In Chemical Formula 1-3,
L¹ and L² are independently a single bond or a linking group selected from —C(R$^x$)=C(R$^y$)— (wherein R$^x$ and R$^y$ are independently hydrogen, a C1 to C20 alkyl group, or a C6 to C30 aryl group), —C≡C—, —O—, —S—, —N(R$^a$)—, —C(=O)—, —C(=O)O—, —OC(=O)—, —SC(=O)—, —C(=O)S—, —N(R$^b$)C(=O)—, and —C(=O)N(R$^c$)— (wherein R$^a$ to R$^c$ is hydrogen, a C1 to C20 alkyl group, or a C6 to C30 aryl group) or a C2 to C20 alkylene group, wherein at least one —(CH₂)— group is replaced by the above linking group selected from —C(R$^x$)=C(R$^y$)—, —C≡C—, —O—, —S—, —N(R$^a$)—, —C(=O)—, —C(=O)O—, —OC(=O)—, —SC(=O)—, —C(=O)S—, —N(R$^b$)C(=O)—, and —C(=O)N(R$^c$)— (wherein R$^x$, R$^y$, and R$^a$ to R$^c$ are the same as described above) in the main chain, a hydrogen bound to each cyclohexylene ring, each phenylene ring, and each naphthylene ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)R$^a$), a substituted or unsubstituted C2 to C20 ester group (—C(=O)OR$^b$), a substituted or unsubstituted C3 to C30 cycloalkyl group, a substituted or unsubstituted C6 to C30 aryl group, —S(=O)R$^c$, —S(=O)OR$^d$, —S(=O)₂R$^e$, or —S(=O)₂OR$^f$ (wherein R$^a$ to R$^f$ are selected from hydrogen, a C1 to C20 alkyl group, and a C6 to C30 aryl group), and at least one non-adjacent —(CH₂)— group of each cyclohexylene ring is optionally replaced by —O—, —S—, or —N(R$^a$)— (wherein R$^a$ is selected from hydrogen, a C1 to C20 alkyl group, and a C6 to C30 aryl group), and at least one non-adjacent =CH— group of each phenylene ring or each naphthylene ring is optionally replaced by =N—.

In Chemical Formula 1 or 2, the polymerizable functional group may be selected from a substituted or unsubstituted C2 to C10 alkenyl group, a substituted or unsubstituted C2 to C10 alkynyl group, a substituted or unsubstituted oxetanyl group, a substituted or unsubstituted (meth)acryl group, a substituted or unsubstituted (meth)acryloyloxy group, a substituted or unsubstituted (meth)acryloylamino group, a substituted or unsubstituted (meth)acryloyl group, a substituted or unsubstituted maleoyl group, a substituted or unsubstituted epoxy alkyl group, and a substituted or unsubstituted epoxy cycloalkyl group.

Examples of the polymerizable functional group may be a functional group represented by Chemical Formula 1-4:

Chemical Formula 1-4

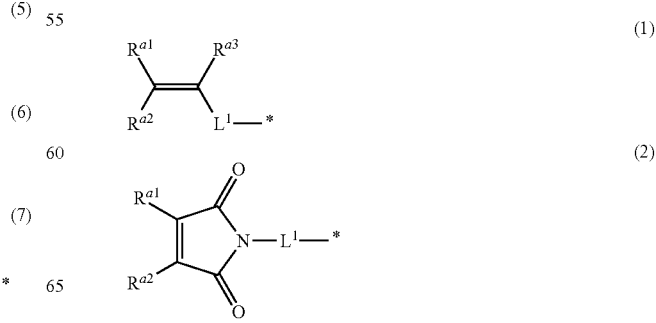

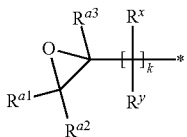

(3)

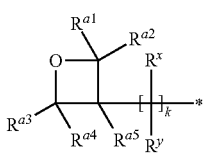

(4)

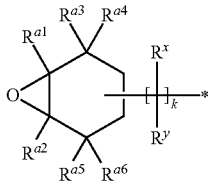

(5)

In Chemical Formula 1-4,

* indicates a site bound to $X^5$ or $X^6$ in Chemical Formula 1, $R^{a1}$, $R^{a2}$, $R^{a3}$, $R^{a4}$, $R^{a5}$, and $R^{a6}$ are independently selected from hydrogen, a halogen, C1 to C6 alkyl group and C1 to C6 haloalkyl group, $L^1$ is a single bond or a linking group selected from —O—, —C(=O)—, —OC(=O)—, and —C(=O)O— or a C2 to C20 alkylene group, wherein at least one —(CH$_2$)— group is replaced by the above the linking group in the main chain, $R^x$ and $R^y$ are independently selected from hydrogen, a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)R$^a$), a substituted or unsubstituted C2 to C20 ester group (—C(=O)OR$^b$), a substituted or unsubstituted C3 to C30 cycloalkyl group, a substituted or unsubstituted C6 to C30 aryl group, —S(=O)R$^c$, —S(=O)OR$^d$, —S(=O)$_2$R$^e$, and —S(=O)$_2$OR$^f$ (wherein $R^a$ to $R^f$ are selected from hydrogen, a C1 to C20 alkyl group, and a C6 to C30 aryl group), and k is an integer of 0 to 10, provided that when k is 2 or more, at least one non-adjacent —(CR$^x$R$^y$)— is optionally replaced by a linking group selected from —O—, —C(=O)—, —OC(=O)—, and —C(=O)O—.

The polymerizable liquid crystal compound may have Δn, which is a difference between a refractive index for extraordinary light and a refractive index for ordinary light, that satisfies Relationship Equation 1.

$$0.05 \leq \Delta n \leq 0.1 \quad \text{Relationship Equation 1}$$

In Relationship Equation 1,

Δn=ne−no, wherein ne denotes a refractive index for extraordinary light, and no denotes a refractive index for ordinary light.

Another embodiment provides a composition for an optical film including the polymerizable liquid crystal compound.

The composition for an optical film may further include a rod-shaped liquid crystal compound.

The composition for an optical film may include the polymerizable liquid crystal compound and the rod-shaped liquid crystal compound in a weight ratio of about 20:80 to about 80:20.

According to another embodiment, an optical film includes:

a substrate, and a liquid crystal layer disposed on one surface of the substrate, wherein the liquid crystal layer includes the composition for an optical film.

The liquid crystal layer may include:

a first liquid crystal layer including the polymerizable liquid crystal compound and a rod-shaped liquid crystal compound, and a second liquid crystal layer including a rod-shaped liquid crystal compound.

The optical film may have forward wavelength dispersion retardation or reverse wavelength dispersion retardation.

According to another embodiment, a compensation film includes:

the optical film, and a retardation film disposed on at least one surface of the optical film.

The retardation film may be a Δ/4 retardation film, a Δ/2 retardation film, or a combination thereof.

According to another embodiment, an antireflective film includes:

the compensation film, and a polarization film disposed on one surface of the compensation film.

According to another embodiment, a display device includes:

a display panel, and the optical film, the compensation film, or the antireflective film.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
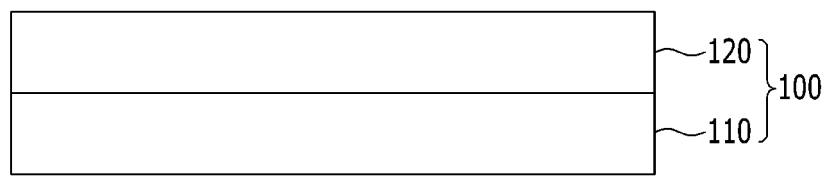
FIG. 1 is a cross-sectional view of an optical film according to an embodiment.

Exemplary embodiments will hereinafter be described in detail, and may be easily performed by those who have common knowledge in the related art. However, this disclosure may be embodied in many different forms and is not construed as limited to the exemplary embodiments set forth herein.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of" when preceding a list of elements, modify the entire list of elements and do not modify the individual elements of the list.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

A part having no relationship with the description is omitted for clarity, and the same or similar constituent element is indicated by the same reference numeral throughout the disclosure.

As used herein, when a definition is not otherwise provided, the term "substituted" may refer to replacement of hydrogen of a compound by a halogen group (—F, —Br, —Cl, or —I), a hydroxy group, a nitro group, a cyano group, an amino group, an azido group, an amidino group, a hydrazino group, a hydrazono group, a carbonyl group, a carbamoyl group, a thiol group, an ester group, a carboxylic acid group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C20 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when a definition is not otherwise provided, the prefix "hetero" may refer to one including 1 to 3 heteroatoms selected from N, O, S, and P.

As used herein, when a definition is not otherwise provided, the term "halogen" may refer to fluorine (F), chlorine (Cl), bromine (Br), or iodine (I).

As used herein, when a definition is not otherwise provided, the term "divalent aliphatic hydrocarbon group" refers to a C1 to C40 alkylene group or a C1 to C30 heteroalkylene group, the term "monovalent aromatic hydrocarbon group" refers to a C6 to C40 aryl group or a C3 to C30 heteroaryl group, the term "divalent aromatic hydrocarbon group" refers to a C6 to C40 arylene group or a C3 to C30 heteroarylene group, the term "trivalent aromatic hydrocarbon group" refers to a trivalent group derived from a C6 to C40 aromatic compound or a C3 to C30 heteroaromatic compound, the term "divalent alicyclic hydrocarbon group" refers to a C3 to C40 cycloalkylene group, a C3 to C40 cycloalkenylene group, a C3 to C40 cycloalkynylene group, a C3 to C40 heterocycloalkylene group, a C3 to C40 heterocycloalkenylene group, or a C3 to C40 heterocycloalkynylene group.

As used herein, when a definition is not otherwise provided, the term "alkyl" group refers to a straight or branched chain saturated aliphatic hydrocarbon group having the specified number of carbon atoms, and having a valence of at least one, optionally substituted with one or more substituents where indicated, provided that the valence of the alkyl group is not exceeded.

As used herein, when a definition is not otherwise provided, the term "haloalkyl" group refers to an alkyl group as defined above, in which one or more hydrogen atoms are substituted with a halogen atom(s) selected from fluorine, chlorine, bromine, or iodine.

As used herein, when a definition is not otherwise provided, the term "alkenyl" group refers to a straight or branched chain hydrocarbon group that comprises at least one carbon-carbon double bond, having the specified number of carbon atoms, and having a valence of at least one, optionally substituted with one or more substituents where indicated, provided that the valence of the alkenyl group is not exceeded.

As used herein, when a definition is not otherwise provided, the term "alkynyl" group refers to a straight or branched chain, monovalent hydrocarbon group having at least one carbon-carbon triple bond, having the specified number of carbon atoms, and having a valence of at least one, optionally substituted with one or more substituents where indicated, provided that the valence of the alkynyl group is not exceeded.

As used herein, when a definition is not otherwise provided, the alkyl group, the alkenyl group, or the alkynyl group may be linear or branched. Examples of the alkyl group may be a methyl group, an ethyl group, an iso-propyl group, a tert-butyl group, a n-octyl group, a n-decyl group, a n-hexadecyl group, and the like. Examples of the alkenyl group may be a vinyl group, an allyl group, a 2-butenyl group, or 3-pentenyl group. Examples of the alkynyl group may be a propargyl group, or a 3-pentynyl group.

As used herein, when a definition is not otherwise provided, the term "cycloalkyl" group refers to a group that comprises one or more saturated and/or partially saturated rings in which all ring members are carbon, such as cyclopropyl, cyclobutyl, cyclopentyl, cyclohexyl, cycloheptyl, cyclooctyl, adamantyl and partially saturated variants of the foregoing, such as cycloalkenyl groups (e.g., cyclohexenyl) or cycloalkynyl groups, and having a valence of at least one, and optionally substituted with one or more substituents where indicated, provided that the valence of the alkyl group is not exceeded.

As used herein, when a definition is not otherwise provided, the term "aryl" group refers to a cyclic group in which all ring members are carbon and at least one ring is aromatic, the group having the specified number of carbon atoms, and having a valence of at least one, optionally substituted with one or more substituents where indicated, provided that the valence of the aryl group is not exceeded, for example a C6 to C30 aryl group, and specifically a C6 to C18 aryl group. More than one ring may be present, and any additional rings may be independently aromatic, saturated or partially unsaturated, and may be fused, pendant, spirocyclic, or a combination thereof.

As used herein, when a definition is not otherwise provided, the term "ketone" group refers to an alkyl group or an aryl group as defined above, having the specified number of carbon atoms, linked to a carbonyl group, e.g. alkyl-C(=O)— or aryl-C(=O)—.

As used herein, when a definition is not otherwise provided, the term "ester" group refers to an alkyl group or an aryl group as defined above, having the specified number of carbon atoms, linked to an oxycarbonyl group, e.g. —C(=O)O-alkyl or —C(=O)—O-aryl.

As used herein, when a definition is not otherwise provided, the term "alkylsulfonyl" group refers to an alkyl group as defined above, having the specified number of carbon atoms, linked via a sulfonyl group, e.g. alkyl-$SO_2$—.

As used herein, when a definition is not otherwise provided, the term "alkylene" group refers to a straight or branched chain, saturated, aliphatic hydrocarbon group having the specified number of carbon atoms, for example a C1 to C30 alkylene group, and specifically a C1 to C18 alkylene group, and having a valence of at least two, optionally substituted with one or more substituents where indicated, provided that the valence of the alkyl group is not exceeded.

As used herein, when a definition is not otherwise provided, the term "amine group" refers to NRR' wherein R and R' are independently hydrogen, a C1 to C20 alkyl group, or a C6 to C30 aryl group.

As used herein, when a definition is not otherwise provided, the term "oxetanyl group" refers to a group derived from a four membered heterocycle including three carbon atoms and one oxygen atom.

As used herein, when a definition is not otherwise provided, the term "(meth)acryl" refers to acryl and/or methacryl, the term "(meth)acryloyl" refers to acryloyl and/or methacryloyl, the term "(meth)acryloyloxy" refers to acryloyloxy and/or methacryloyloxy, and the term "(meth)acryloylamino" refers to acryloylamino and/or methacryloylamino.

As used herein, when a definition is not otherwise provided, the term "maleoyl" refers to (Z)-alkyl-O—C(=O)—CH=CH—C(=O)— or (Z)-aryl-O—C(=O)—CH=CH—C(=O)—, wherein the alkyl group and the aryl group are the same as defined above.

As used herein, when a definition is not otherwise provided, the term "epoxy alkyl group" refers to an alkyl group as defined above, which contains a three-membered ring including two carbon atoms and one oxygen atom.

As used herein, when a definition is not otherwise provided, the term "epoxy cycloalkyl group" refers to a cycloalkyl group as defined above, which contains a three-membered ring including two carbon atoms and one oxygen atom.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent.

For example, when the term "substituted C1 to C20 alkyl" refers to a C1 to C20 alkyl group substituted with a C6 to C20 aryl group, the total number of carbon atoms in the resulting aryl substituted alkyl group is C7 to C40.

Hereinafter, a polymerizable liquid crystal compound according to an embodiment is described.

A polymerizable liquid crystal compound according to an embodiment is represented by Chemical Formula 1.

Chemical Formula 1

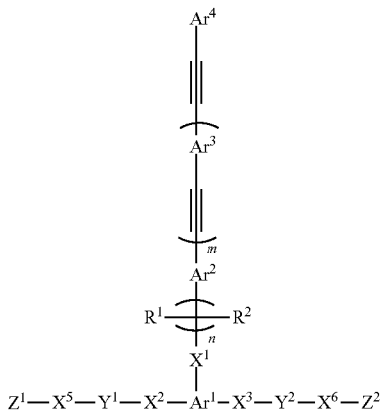

In Chemical Formula 1, $Ar^1$ is a substituted or unsubstituted trivalent aromatic hydrocarbon group, $Ar^2$ and $Ar^3$ are independently a substituted or unsubstituted divalent aromatic hydrocarbon group, $Ar^4$ is a substituted or unsubstituted monovalent aromatic hydrocarbon group, $X^1$ is selected from —C(=O)O— and —C(=O)N($R^a$)— (wherein $R^a$ is hydrogen, a C1 to C20 alkyl group, or a C6 to C30 aryl group), $R^1$ and $R^2$ are independently selected from hydrogen, a halogen, a cyano group, a nitro group, an aldehyde group, a ketone group (—C(C=O)R, wherein R is a C1 to C20 alkyl group or a C6 to C30 aryl group), an ester group (—C(C=O)OR, wherein R is a C1 to C20 alkyl group or a C6 to C30 aryl group), an alkylsulfonyl group (—C(S=O)$_2$R, wherein R is a C1 to C20 alkyl group or a C6 to C30 aryl group), and a substituted or unsubstituted C1 to C20 alkyl group, n is an integer of 0 to 2, m is 1 or 2, $X^2$ and $X^3$ are independently selected from —OC(=O)—, —C(=O)O—, —N($R^a$)C(=O)—, and —C(=O)N($R^a$)— (wherein $R^a$ is hydrogen, a C1 to C20 alkyl group, or a C6 to C30 aryl group), $Y^1$ and $Y^2$ are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof, $X^5$ and $X^6$ are independently a linking group selected from —OC(=O)—, —C(=O)O—, —S—, —O—, —S(=O)—, —C(=O)—, —S(=O)$_2$—, —N($R^a$)—, —C(=O)S—, —N($R^b$)C(=O)—, and —C(=O)N($R^c$)— (wherein $R^a$, $R^b$, and $R^c$ are independently selected from hydrogen, a C1 to C20 alkyl group, and a C6 to C30 aryl group), or a C2 to C20 alkylene group, wherein at least one —(CH$_2$)— group is replaced by the above linking group in the main chain, and $Z^1$ and $Z^2$ are independently a C2 to C30 polymerizable functional group. The polymerizable liquid crystal compound of Chemical Formula 1 is a T-shaped mesogenic compound having $Ar^1$ as a core group, a bistolane (1,4-bis(phenylethynyl)benzene) moiety as a lateral group, and a polymerizable functional group at both sides. When the direction of a nematic director including the $Ar^1$ is regarded as an x-axis, the lateral group may be aligned along a z-axis or two-dimensionally along a y-axis.

The polymerizable liquid crystal compound has excellent solubility in an organic solvent, miscibility, and coating properties as well as satisfactory liquid crystallinity and optical anisotropy. Thus, these properties may improve film processability. In addition, the polymerizable liquid crystal compound may provide a film having a reverse wavelength dispersion retardation as well as a forward wavelength dispersion retardation. Accordingly, the film including the polymerizable liquid crystal compound of Chemical Formula 1 may be appropriately used as an optical film and as a Δ/4 plate (a quarter wave film).

The polymerizable liquid crystal compound represented by Chemical Formula 1 may be represented by Chemical Formula 2.

Chemical Formula 2

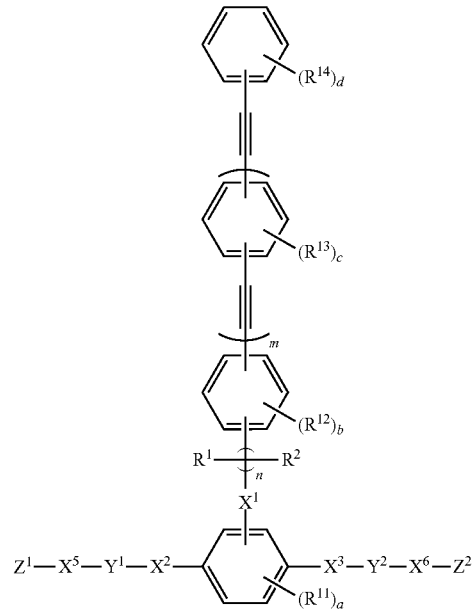

In Chemical Formula 2, $X^1$ is selected from —C(=O)O— and —C(=O)N($R^a$)— (wherein $R^a$ is hydrogen, a C1 to C20 alkyl group, or a C6 to C30 aryl group), $R^1$ and $R^2$ are independently selected from hydrogen, a halogen, a cyano group, a nitro group, an aldehyde group, a ketone group (—(C=O)R, wherein R is a C1 to C20 alkyl group or a C6 to C30 aryl group), an ester group (—(C=O)OR, wherein R is a C1 to C20 alkyl group or a C6 to C30 aryl group), an alkylsulfonyl group (—(S=O)$_2$R, wherein R is a C1 to C20 alkyl group or a C6 to C30 aryl group), and a substituted or unsubstituted C1 to C20 alkyl group, n is an integer of 0 to 2, m is 1 or 2, $R^{11}$, $R^{12}$, $R^{13}$, and $R^{14}$ are independently selected from hydrogen, a halogen, a cyano group, a nitro group, an aldehyde group, and a substituted or unsubstituted C1 to C20 alkyl group, a, b, c, and d are independently determined according to the valence of phenylene, for example a is an integer of 0 to 3 b, c, and d are independently integers of 0 to 4.

$X^2$ and $X^3$ are independently selected from —OC(=O)—, —C(=O)O—, —N(R$^a$)C(=O)—, and —C(=O)N(R$^a$)— (wherein R$^a$ is hydrogen, a C1 to C20 alkyl group, or a C6 to C30 aryl group), $Y^1$ and $Y^2$ are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof, $X^5$ and $X^6$ are independently a linking group selected from —OC(=O)—, —C(=O)O—, —S—, —O—, —S(=O)—, —C(=O)—, —S(=O)$_2$—, —N(R$^a$)—, —C(=O)S—, —N(R$^b$)C(=O)—, and —C(=O)N(R$^c$)— (wherein R$^a$, R$^b$, and R$^c$ are independently selected from hydrogen, a C1 to C20 alkyl group, and a C6 to C30 aryl group), or a C2 to C20 alkylene group, wherein at least one —(CH$_2$)— group is replaced by the above linking group in the main chain, and $Z^1$ and $Z^2$ are independently a C2 to C30 polymerizable functional groups.

The Ar$^1$ may be an aromatic hydrocarbon group represented by Chemical Formula 1-1.

Chemical Formula 1-1

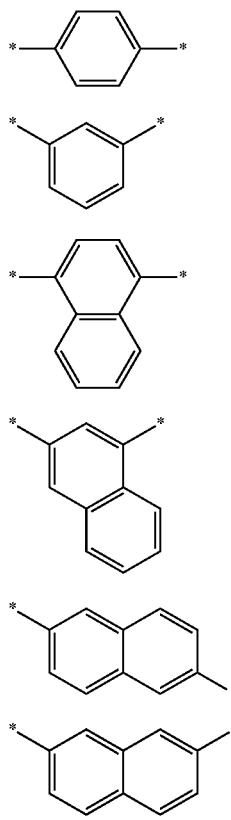

(1)
(2)
(3)
(4)
(5)
(6)

In Chemical Formula 1-1, a hydrogen bound to each aromatic ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)R$^a$), a substituted or unsubstituted C2 to C20 ester group (—C(=O)OR$^b$), a substituted or unsubstituted C3 to C30 cycloalkyl group, a substituted or unsubstituted C6 to C30 aryl group, —S(=O)R$^c$, —S(=O)OR$^d$, —S(=O)$_2$R$^e$, or —S(=O)$_2$OR$^f$ (wherein R$^a$ to R$^f$ are selected from hydrogen, a C1 to C20 alkyl group, and a C6 to C30 aryl group), at least one =CH— group of each aromatic ring is optionally replaced by =N—, and two asterisks indicates linking points bound to $X^2$ and $X^3$.

The polymerizable liquid crystal compound stably maintains a T-shape due to an aromatic hydrocarbon group present at the Ar$^1$ position, and —C(=O)O— or —C(=O)N(R$^a$)— present at the $X^1$ position. For example, when alkylene or cycloalkylene group is present in the Ar$^1$ position, or when a linking group other than C(=O)O— or —C(=O)N(R$^a$)— is present at the $X^1$ position, the T-shape may not be stably maintained.

In addition, when $X^2$ and $X^3$ are —OC(=O)—, —C(=O)O—, —N(R$^a$)C(=O)—, or —C(=O)N(R$^a$)—, free rotation between Ar$^1$ of the nematic director and $X^2$, and between the Ar$^1$ and $X^3$ may be suppressed, and thus structural stability of the T-shape may be provided. When a freely rotatable linking group is introduced into the $X^2$ and $X^3$, the structural stability of the T-shape may not be obtained.

In addition, when the $X^2$ and $X^3$ including a carbonyl group are adjacent to an aromatic hydrocarbon group present at the Ar$^1$ position, the length of consecutive double bonds is increased, and absorption of light at a long wavelength may be strongly improved.

In Chemical Formula 1, —C(R$^1$)(R$^2$)— as a substituted or unsubstituted methylene group may provide structural variability to the polymerizable liquid crystal compound, and solubility in an organic solvent, miscibility with other compounds, and molecular flexibility may be improved. A bistolane lateral group is rotated to a degree with the —C(R$^1$)(R$^2$)— as the center, thus applying flexibility to the bistolane lateral group. As a result, steric hindrance with neighboring molecules may be decreased.

In Chemical Formula 1, examples of the —C(R$^1$)(R$^2$)— may be a functional group represented by Chemical Formula 1-2:

Chemical Formula 1-2

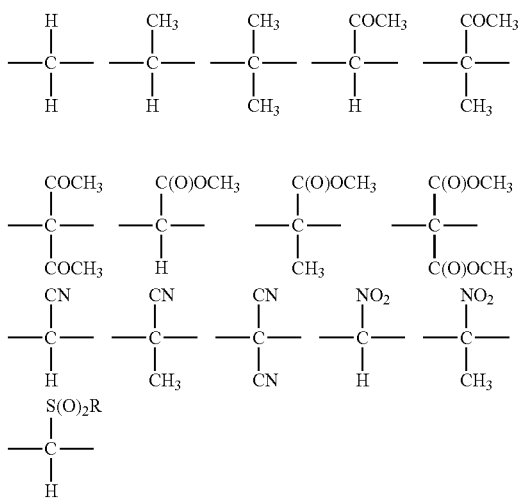

In Chemical Formula 1-2,

R is selected from a C1 to C20 alkyl group and a C6 to C30 aryl group.

The $Y^1$ and $Y^2$ may independently be a functional group represented by Chemical Formula 1-3:

Chemical Formula 1-3

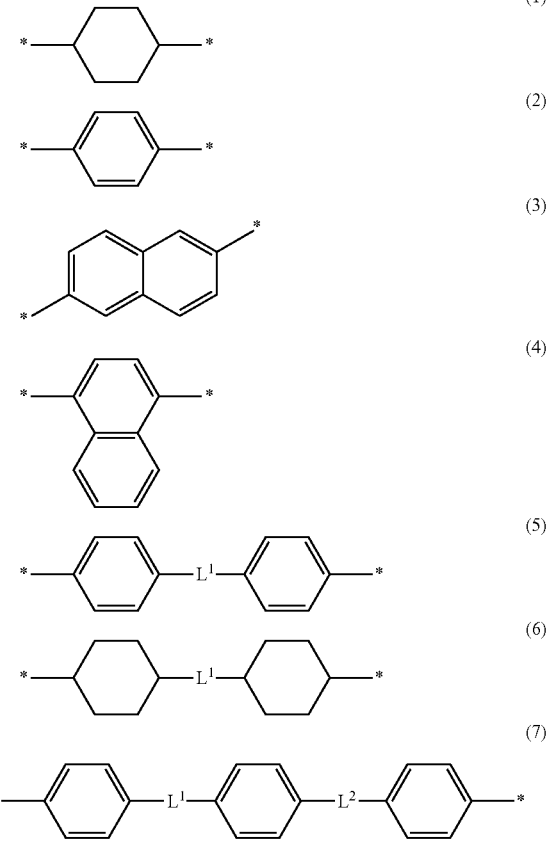

In Chemical Formula 1-3, $L^1$ and $L^2$ are independently a single bond or a linking group selected from —C($R^x$)=C($R^y$)— (wherein $R^x$ and $R^y$ are independently hydrogen, a C1 to C20 alkyl group, or a C6 to C30 aryl group), —C≡C—, —O—, —S—, —N($R^a$)—, —C(=O)—, —C(=O)O—, —OC(=O)—, —SC(=O)—, —C(=O)S—, —N($R^b$)C(=O)—, and —C(=O)N($R^c$)— (wherein $R^a$ to $R^c$ is hydrogen, a C1 to C20 alkyl group, or a C6 to C30 aryl group) or a C2 to C20 alkylene group, wherein at least one —(CH$_2$)— group is replaced by the above linking group selected from —C($R^x$)=C($R^y$)—, —C≡C—, —O—, —S—, —N($R^a$)—, —C(=O)—, —C(=O)O—, —OC(=O)—, —SC(=O)—, —C(=O)S—, —N($R^b$)C(=O)—, and —C(=O)N($R^c$)— (wherein $R^x$, $R^y$, and $R^a$ to $R^c$ are the same as described above) in the main chain, a hydrogen bound to each cyclohexylene ring, each phenylene ring, and each naphthylene ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)$R^a$), a substituted or unsubstituted C2 to C20 ester group (—C(=O)O$R^b$), a substituted or unsubstituted C3 to C30 cycloalkyl group, a substituted or unsubstituted C6 to C30 aryl group, —S(=O)$R^c$, —S(=O)O$R^d$, —S(=O)$_2R^e$, or —S(=O)$_2$O$R^f$ (wherein $R^a$ to $R^f$ are selected from hydrogen, a C1 to C20 alkyl group, and a C6 to C30 aryl group), and at least one non-adjacent —(CH$_2$)— group of each cyclohexylene ring is optionally replaced by —O—, —S—, or —N($R^a$)— (wherein $R^a$ is selected from hydrogen, a C1 to C20 alkyl group, and a C6 to C30 aryl group), and at least one non-adjacent =CH— group of each phenylene ring or each naphthalene ring is optionally replaced by =N—.

When the $Y^1$ and $Y^2$ has a ring structure such as a substituted or unsubstituted divalent aromatic hydrocarbon group or a substituted or unsubstituted divalent alicyclic hydrocarbon group, $X^2$ and $X^3$ and $X^5$ and $X^6$ may be bound to each $Y^1$ and $Y^2$ at a meta position or a para position.

In Chemical Formula 1 or 2, the polymerizable functional group may be selected from a substituted or unsubstituted C2 to C10 alkenyl group, a substituted or unsubstituted C2 to C10 alkynyl group, a substituted or unsubstituted oxetanyl group, a substituted or unsubstituted (meth)acryl group, a substituted or unsubstituted (meth)acryloyloxy group, a substituted or unsubstituted (meth)acryloylamino group, a substituted or unsubstituted (meth)acryloyl group, a substituted or unsubstituted maleoyl group, a substituted or unsubstituted epoxy alkyl group, and a substituted or unsubstituted epoxy cycloalkyl group.

The polymerizable liquid crystal compound may have Δn, which is a difference between a refractive index for extraordinary light and a refractive index for ordinary light, that satisfies Relationship Equation 1.

$$0.05 \leq \Delta n \leq 0.1 \quad \text{Relationship Equation 1}$$

In Relationship Equation 1,

Δn=ne−no, wherein ne denotes a refractive index for extraordinary light, and no denotes a refractive index for ordinary light. While not wishing to be bound by theory, it is understood that when the Δn is within this range, in-plane retardation may be generated.

Another embodiment provides a composition for an optical film including the polymerizable liquid crystal compound.

The composition for an optical film may further include a rod-shaped liquid crystal compound.

The rod-shaped liquid crystal compound may include, for example at least one of a rod-shaped aromatic derivative having at least one C2 to C30 polymerizable functional group, 1-methyl propylene glycol, propylene glycol 2-acetate, and a compound represented by $P^1$-$A^1$-($Y^1$-$A^2$)$_n$-$P^2$ (wherein at least one of $P^1$ and $P^2$ includes a C2 to C30 polymerizable functional group, for example an acrylate group, a methacrylate group, an acryloyl group, a methacryloyl group, a vinyl group, a vinyloxy group, an epoxy alkyl group, or a combination thereof, $A^1$ and $A^2$ independently include 1,4-phenylene, a naphthalene-2,6-diyl group, or a combination thereof, $Y^1$ is a single bond, —C(=O)O—, —OC(=O)—, or a combination thereof, and n is 0, 1 or 2), but is not limited thereto.

The composition for an optical film may include the polymerizable liquid crystal compound and the rod-shaped liquid crystal compound in a weight ratio of about 10:90 to 90:10, for example, about 20:80 to about 80:20. While not wishing to be bound by theory, it is understood that within these ranges, an optical film having forward wavelength dispersion retardation or reverse wavelength dispersion retardation may be provided.

For example, the rod-shaped liquid crystal compound may include at least one of a first rod-shaped liquid crystal compound represented by Chemical Formula 3-1, a second rod-shaped liquid crystal compound represented by Chemical Formula 3-2, and a third rod-shaped liquid crystal compound represented by Chemical Formula 3-3.

Chemical Formula 3-1

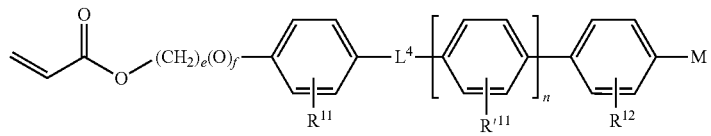

Chemical Formula 3-2

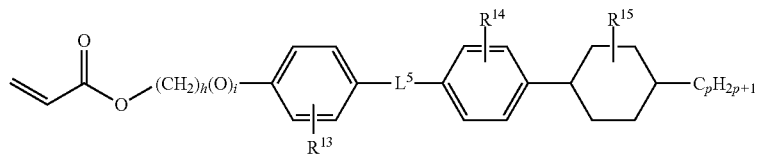

Chemical Formula 3-3

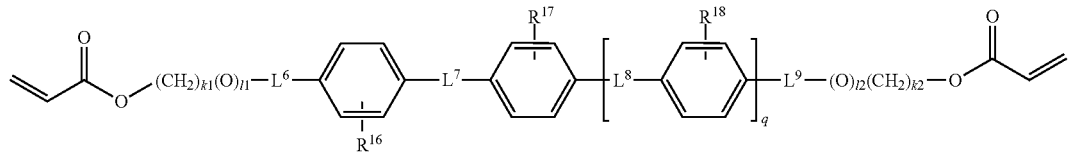

In Chemical Formulae 3-1 to 3-3,

M is a cyano group, a cyano-containing group, a hydroxy group, a substituted or unsubstituted carboxylic acid group, or a combination thereof, $R^{11}$, $R'^{11}$, and $R^{12}$ to $R^{18}$ are independently hydrogen, a substituted or unsubstituted C1 to C10 alkyl group, a substituted or unsubstituted C1 to C10 alkoxy group, a halogen atom, a halogen-containing group, or a combination thereof, $L^4$ to $L^9$ are independently selected from a C3 to C10 alkylene group, wherein at least one —($CH_2$)— group is replaced by the above linking group selected from a single bond, —C(=O)O—, —OC(=O)—, —C(=O)O—, —OC(=O)—, and a combination thereof, e, h, p, $k_1$, and $k_2$ are independently integers of 1 to 10, and n, f, i, $l_1$, $l_2$, and q are independently 0 or 1.

Two or more of the rod-shaped liquid crystal compound may be combined (for instance, mixed).

For example, the mixture may include the first rod-shaped liquid crystal compound and the second rod-shaped liquid crystal compound in an amount, for example, about 10 percent by weight (wt %) to about 90 wt % of the first rod-shaped liquid crystal compound and about 10 wt % to about 90 wt % of the second rod-shaped liquid crystal compound based on the total amount of the rod-shaped liquid crystal compound. At least one of the first rod-shaped liquid crystal compound and the second rod-shaped liquid crystal compound may be combined with the third rod-shaped liquid crystal compound in an amount, for example, about 10 wt % to about 90 wt % of at least one of the first rod-shaped liquid crystal compound and the second rod-shaped liquid crystal compound and about 10 wt % to about 90 wt % of the third rod-shaped liquid crystal compound based on the total amount of the rod-shaped liquid crystal compound.

The polymerizable liquid crystal compound alone or a mixture of the polymerizable liquid crystal compound and the rod-shaped liquid crystal compound may be included in an amount of about 5 wt % to about 50 wt %, for example, about 5 wt % to about 40 wt %, for example, about 10 wt % to about 35 wt %, based on the total amount of the composition for an optical film. While not wishing to be bound by theory, it is understood that within these ranges, optical properties of the optical film may be effectively ensured.

The composition for an optical film may further include a reaction initiator. The reaction initiator may be, for example a photoinitiator, for example a free radical photoinitiator and/or an ionic photoinitiator.

The reaction initiator may be included in an amount of about 0.01 wt % to about 5 wt %, for example, about 0.1 wt % to about 4 wt %, or about 0.1 wt % to about 2 wt %, based on the total amount of the composition for an optical film. While not wishing to be bound by theory, it is understood that within these ranges, reactivity may be effectively increased.

The composition for an optical film may further include an additive. The additive may be a surfactant, a dissolution aid, and/or a dispersing agent, but is not limited thereto.

The composition for an optical film may further include a solvent that may dissolve and/or disperse the above components. The solvent may not be particularly limited as long as it does not cause physical or chemical damage to the substrate. The solvent may be, for example, at least one selected from deionized water, methanol, ethanol, propanol, iso-propanol, 2-methoxyethanol, 2-ethoxyethanol, 2-propoxyethanol 2-butoxyethanol, methylcellosolve, ethylcellosolve, butylcellosolve, diethylene glycol methyl ether, diethylene glycol ethyl ether, dipropylene glycol methyl ether, toluene, xylene, hexane, heptane, octane, ethyl acetate, butyl acetate, diethylene glycol dimethyl ether, diethylene glycol dimethyl ethyl ether, methyl ethoxy propionate, ethyl ethoxy propionate, ethyl lactate, propylene glycol methyl ether acetate, propylene glycol methyl ether, propylene glycol propyl ether, methylcellosolve acetate, ethylcellosolve acetate, diethylene glycol methyl acetate, diethylene glycol ethyl acetate, acetone, methyl ethyl ketone, methyl iso-butyl ketone, cyclopentanone, cyclohexanone, dimethyl formamide (DMF), N,N-dimethyl acetamide (DMAc), N-methyl-2-pyrrolidone (NMP), γ-butyrolactone, diethyl ether, ethylene glycol dimethyl ether, diglyme, tetrahydrofuran (THF), acetylacetone, acetonitrile, chloroform, dichloromethane, tetrachloroethane, trichloroethylene, tetrachloroethylene, chlorobenzene, benzene, toluene, and xylene. The solvent may be a single solvent or a mixed solvent.

The solvent may be included in a balance amount other than the above components based on the total amount of the composition for an optical film.

The composition for an optical film may be coated on a substrate and dried to manufacture an optical film.

The substrate may be, for example a glass substrate, a metal substrate, a semiconductor substrate, or a polymer substrate, and the polymer substrate may be, for example a substrate made of polyethylene terephthalate (PET), polyvinyl alcohol (PVA), polycarbonate (PC), triacetyl cellulose (TAC), a derivative thereof, and/or a combination thereof, but is not limited thereto.

The composition for an optical film may be, for example coated using a solution process such as spin coating, slit coating, and/or inkjet coating, and a thickness of a film may be controlled considering a refractive index of a film.

The coated composition for an optical film may be, for example dried at a temperature of greater than or equal to a boiling point of the solvent.

Hereinafter, an optical film formed using the composition for an optical film is described with reference to drawings.

FIG. 1 is a cross-sectional view of an optical film according to an embodiment.

Referring to FIG. 1, an optical film 100 according to an embodiment includes a substrate 110 and a liquid crystal layer 120 disposed on one surface of the substrate 110.

The substrate 110 may be, for example a glass substrate, a metal substrate, a semiconductor substrate, or a polymer substrate. The polymer substrate a substrate made of, for example, polyethylene terephthalate (PET), polyvinyl alcohol (PVA), polycarbonate (PC), triacetyl cellulose (TAC), a derivative thereof, and/or a combination thereof, but is not limited thereto. When the optical film 100 includes another lower layer besides the substrate 110, the substrate 110 may be the lower layer. The substrate 110 may be omitted as needed.

The liquid crystal layer 120 may include the polymerizable liquid crystal compound alone or a mixture of the polymerizable liquid crystal compound and the rod-shaped liquid crystal compound.

The liquid crystal compounds may have an optical axis, which is tilted with respect to the surface of the liquid crystal layer 120. Herein, the tilting with respect to the surface of the liquid crystal layer 120 means that the liquid crystal compounds are not perpendicularly or horizontally aligned with respect to a length direction of the liquid crystal layer 120, and an optical axis of each liquid crystal compound may be tilted at an angle of greater than about 0° and less than 90° with respect to the length direction of the liquid crystal layer 120. A maximum tilt angle of the polymerizable liquid crystal compound may be about 30° to about 70°.

The liquid crystal layer 120 may have a forward wavelength dispersion retardation or a reverse wavelength dispersion retardation. The retardation may be expressed as an in-plane retardation ($R_e$), and the in-plane retardation ($R_e$) may be expressed by $R_e = (n_x - n_y)d$. Herein, $n_x$ is a refractive index in a direction having a largest refractive index in a plane (hereinafter referred to as a "slow axis") of the liquid crystal layer 120, $n_y$ is a refractive index in a direction having a smallest refractive index in a plane (hereinafter referred to as a "fast axis") of the liquid crystal layer 120, and d is a thickness of the liquid crystal layer 120.

Herein, forward wavelength dispersion retardation indicates that a retardation about light at a short wavelength is larger than a retardation about light at a long wavelength, and the in-plane retardation ($R_e$) of the liquid crystal layer 120 for a 450 nanometer (nm) wavelength, a 550 nm wavelength, and a 650 nm wavelength may satisfy, for example Relationship Equation 2.

$$R_e(450 \text{ nm}) > R_e(550 \text{ nm}) > R_e(650 \text{ nm}) \quad \text{Relationship Equation 2}$$

In Relationship Equation 2,
$R_e$ (450 nm) is in-plane retardation for incident light at a 450 nm wavelength,
$R_e$ (550 nm) is in-plane retardation for incident light at a 550 nm wavelength, and
$R_e$ (650 nm) is in-plane retardation for incident light at a 650 nm wavelength.

The reverse wavelength dispersion retardation has larger retardation to light having a long wavelength than retardation to light having a short wavelength, and the in-plane retardation ($R_e$) of the liquid crystal layer 120 for a 450 nm wavelength, a 550 nm wavelength, and a 650 nm wavelength may satisfy, for example Relationship Equation 3.

$$R_e(450 \text{ nm}) < R_e(550 \text{ nm}) < R_e(650 \text{ nm}) \quad \text{Relationship Equation 3}$$

In Relationship Equation 3,
$R_e$ (450 nm) is in-plane retardation for incident light at a 450 nm wavelength,
$R_e$ (550 nm) is in-plane retardation for incident light at a 550 nm wavelength, and
$R_e$ (650 nm) is in-plane retardation for incident light at a 650 nm wavelength.

Short wavelength dispersion may be expressed by the changing of the retardation of the short wavelength relative to the reference wavelength of the liquid crystal layer 120 may satisfy, for example Relationship Equation 4.

$$0.70 \leq R_e(450 \text{ nm})/R_e(550 \text{ nm}) \leq 1.30 \quad \text{Relationship Equation 4}$$

For example, the short wavelength dispersion of the liquid crystal layer 120 may satisfy, for example Relationship Equation 4a.

$$0.72 \leq R_e(450 \text{ nm})/R_e(550 \text{ nm}) \leq 1.20 \quad \text{Relationship Equation 4a}$$

Long wavelength dispersion may be expressed by the changing of the retardation of the long wavelength relative to the reference wavelength, the long wavelength dispersion of the liquid crystal layer 120 may satisfy, for example Relationship Equation 5.

$$0.70 \leq R_e(650 \text{ nm})/R_e(550 \text{ nm}) \leq 1.30 \quad \text{Relationship Equation 5}$$

For example, the long wavelength dispersion of the liquid crystal layer 120 may satisfy, for example Relationship Equation 5a.

$$0.72 \leq R_e(650 \text{ nm})/R_e(550 \text{ nm}) \leq 1.20 \quad \text{Relationship Equation 5a}$$

The liquid crystal layer 120 may realize flat wavelength dispersion retardation that has little changes in in-plane retardation for a 450 nm wavelength, a 550 nm wavelength, and a 650 nm wavelength, and thus may realize reverse wavelength dispersion retardation as well as forward wavelength dispersion retardation. Herein, little changes means that a difference of in-plane retardations in 450 nm and 550 nm and/or a difference of in-plane retardations in 650 nm and 550 nm is within about 10 nm, for example within about 5 nm.

An alignment layer may be disposed between the substrate 110 and the liquid crystal layer 120. The alignment layer may impart a pretilt angle to the liquid crystal compound of the liquid crystal layer 120, thus controlling alignment of the liquid crystal compound on the substrate 110, and may be made of, for example polyamic acid, polyimide, or a combination thereof. The surface of the alignment layer may have a plurality of grooves formed through a physical treatment such as rubbing on the surface or a photo-treatment such as photo-alignment.

The optical film 100 may be formed in a plural layer, and may include a first liquid crystal layer including the polymerizable liquid crystal compound and a rod-shaped liquid crystal compound and a second liquid crystal layer including a rod-shaped liquid crystal compound. The order of the first liquid crystal layer and the second liquid crystal layer is not particularly limited. For example, the first liquid crystal layer may be disposed on the substrate 110 and the second liquid crystal layer may be disposed on the first liquid crystal layer.

The optical film 100 may be used alone or may be used by stacking the same with another film having a different refractive index.

Hereinafter, a compensation film according to an embodiment is described with reference to FIG. 2 along with FIG. 1.

Figure 2:
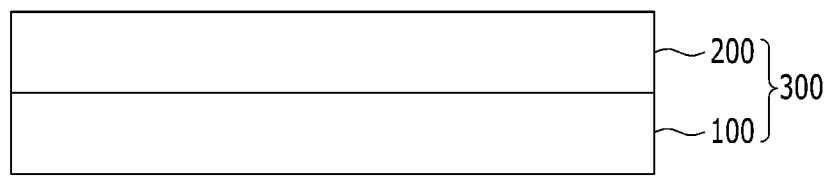
FIG. 2 is a schematic cross-sectional view of a compensation film according to an embodiment.

FIG. 2 is a schematic cross-sectional view of a compensation film according to an embodiment.

A compensation film 300 according to an embodiment includes the optical film 100 and a retardation film 200.

The optical film 100 includes the substrate 110 and the liquid crystal layer 120 as described above. The liquid crystal layer 120 includes the polymerizable liquid crystal compound alone or the mixture of the polymerizable liquid crystal compound and the rod-shaped liquid crystal compound. The liquid crystal layer 120 may include a plurality of liquid crystal layer. Details for the optical film 100 are the same as described above.

The retardation film 200 may be a monolayer or a plural layer, and may be a film having a different refractive index from the optical film 100. The retardation film 200 may be, for example a Δ/4 retardation film, a Δ/2 retardation film, or a combination thereof, but is not limited thereto. Herein, the Δ/4 retardation film may be, for example a film having an in-plane retardation of about 120 nm to about 160 nm for incident light at a 550 nm wavelength and the Δ/2 retardation film may be, for example a film having an in-plane retardation of about 240 nm to about 320 nm for incident light at a 550 nm wavelength.

The compensation film 300 may further include an adhesion layer (not shown) disposed between the optical film 100 and the retardation film 200. The adhesion layer is used to effectively attach the optical film 100 to the retardation film 200, and may be made of, for example, a pressure sensitive adhesive.

The compensation film 300 may have a different refractive index from the optical film 100 and the retardation film 200 by combining refractive indices of the optical film 100 and the retardation film 200.

The compensation film 300 may be prepared to have a desirable retardation by controlling each refractive index and thickness of the optical film 100 and the retardation film 200. For example, the optical film 100 may reduce or offset thickness direction retardation of the retardation film 200, thereby decreasing viewing angle dependency and wavelength dependency to provide a compensation film 300 having a reinforced compensation function. The compensation film 300 may realize a compensation function for circularly polarized light and may improve display characteristics of a display device including such a compensation film 300.

The compensation film 300 may be obtained by respectively manufacturing the optical film 100 and the retardation film 200 in a film shape and then bonding them together, by coating the optical film 100 on the retardation film 200, or coating the retardation film 200 on the optical film 100. The optical film 100 may be manufactured in a film shape by coating the aforementioned composition on the substrate 110 and cross-linking it by irradiation. The compensation film 300 may be formed, for example, in a method of roll-to-roll, spin coating, transfer, and the like, but is not limited thereto.

Figure 3:
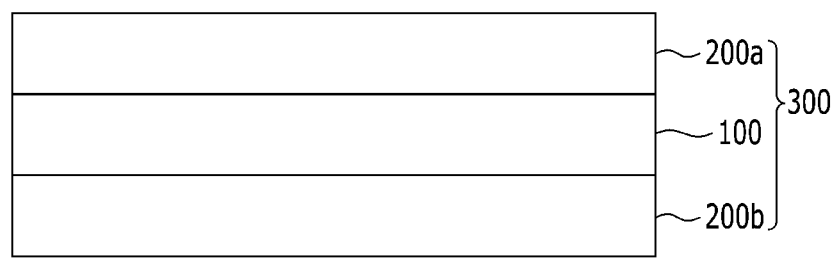
FIG. 3 is a schematic cross-sectional view of a compensation film according to another embodiment.

FIG. 3 is a schematic cross-sectional view showing a compensation film according to another embodiment.

The compensation film 300 according to the present embodiment includes the retardation films 200a and 200b disposed on respective surfaces of the optical film 100, in contrast to the above embodiment.

The compensation film 300 may have a different refractive index from those of the optical film 100 and the retardation films 200a and 200b by combining the refractive indices of the optical film 100 and the retardation films 200a and 200b. The compensation film 300 may be prepared to have desirable retardation by controlling each refractive index and thickness of the optical film 100 and the retardation films 200a and 200b.

The compensation film 300 may further include an adhesion layer (not shown) disposed at at least one of between the optical film 100 and the phase retardation film 200a and between the optical film 100 and the phase retardation film 200b. The adhesion layer effectively adheres between the optical film 100 and the phase retardation films 200a and 200b, and may be, for example, made of a pressure sensitive adhesive.

The compensation film 300 may form an antireflective film with a polarization film that may have an external light antireflection function.

Figure 4:
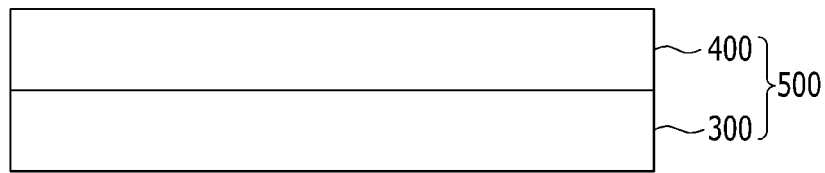
FIG. 4 is a schematic cross-sectional view of an antireflective film according to an embodiment.

FIG. 4 is a schematic cross-sectional view showing an antireflective film according to an embodiment.

Referring to FIG. 4, an antireflective film 500 according to an embodiment includes a compensation film 300 and a polarization film 400 disposed on one surface of the compensation film 300.

The polarization film 400 may be disposed on one surface of the optical film 100, or may be disposed on one surface of the retardation film 200.

The polarization film 400 may be disposed on the side where the light enters, and may be a linear polarizer shifting the polarization of incident light into linear polarization. The polarization film 400 may be made of, for example, elongated polyvinyl alcohol (PVA) according to a method of, for example, drawing a polyvinyl alcohol film, adsorbing iodine or a dichroic dye thereto, and borating and washing the same. The polarization film 400 may be a polarizing film prepared, for example, by mixing a polymer and a dichroic dye and melt blending the polymer with the dichroic dye to melt them at a temperature above the melting point of the polymer.

The antireflective film 500 may further include a protective layer (not shown) disposed on one surface of the polarization film 400. The protective layer may be provided for further reinforcing the functionality or improving the durability of the antireflective film 500, or for reducing reflection or glare, and for example, may be a triacetyl cellulose (TAC) film, but is not limited thereto.

The antireflective film 500 may further include a correction layer (not shown) disposed on one surface of the compensation film 300. The correction layer may be, for example, a color shift resistant layer, but is not limited thereto.

The antireflective film 500 may further include a light blocking layer (not shown) extended along the edge. The light blocking layer may be formed as a strip along the circumference of the antireflective film 500. The light blocking layer may include an opaque material, for example, a black material. For example, the light blocking layer may be made of a black ink.

The antireflective film 500 may be stacked with the compensation film 300 and the polarization film 400 by a roll-to-roll method, without limitation.

Figure 5:
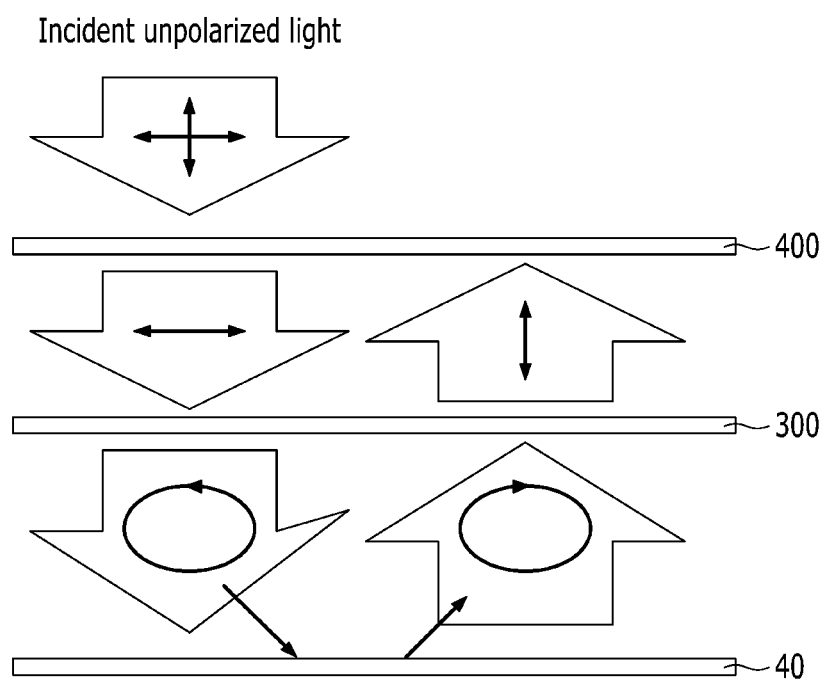
FIG. 5 is a schematic view showing an antireflection principle of an antireflection film according to an embodiment.

FIG. 5 is a schematic view showing the external light anti-reflection principle of an antireflective film according to an embodiment.

Referring to FIG. 5, while the incident unpolarized light having entered (hereinafter, referred to as "external light") from the outside is passed through the polarization film 400, and the polarized light is shifted into circularly polarized light by passing through the compensation film 300, only a first polarized perpendicular component, which is one polarized perpendicular component of two polarized perpendicular components, is transmitted. While the circularly polarized light is reflected in a display panel 40 including a substrate, an electrode, and so on, and changes the circular polarization direction, and while the circularly polarized light is passed through the compensation film 300 again, only a second polarized perpendicular component, which is the other polarized perpendicular component of the two polarized perpendicular components, may be transmitted. As the second polarized perpendicular component is not passed through the polarization film 400, and light does not exit to the outside, effects of preventing the external light reflection may be provided.

The optical film 100, the compensation film 300, or the antireflective film 500 may be applied to various display devices.

A display device according to an embodiment includes a display panel and a film disposed on one surface of the display panel. The display panel may be a liquid crystal panel or an organic light emitting panel, but is not limited thereto. The film may be the optical film 100, the compensation film 300, or the antireflective film 500.

Hereinafter, an organic light emitting display is described as an example of a display device.

Figure 6:
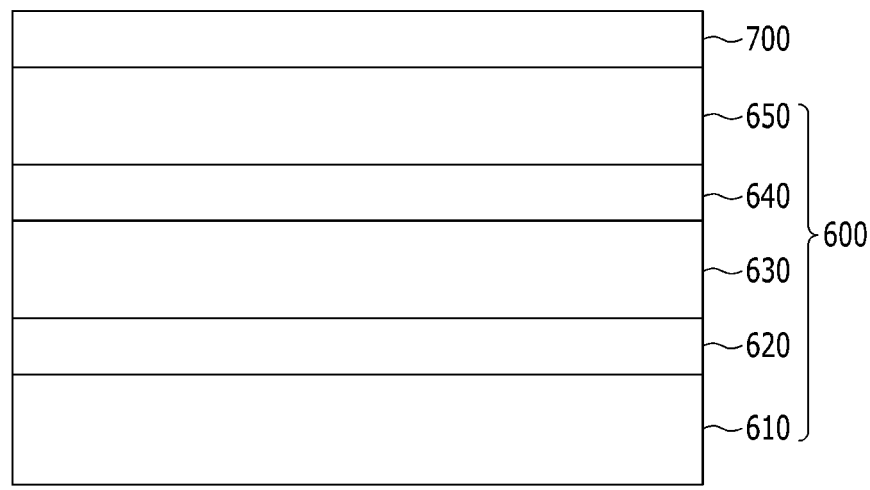
FIG. 6 is a schematic cross-sectional view of an organic light emitting display device according to an embodiment.

FIG. 6 is a schematic cross-sectional view showing an organic light emitting display according to an embodiment.

Referring to FIG. 6, the organic light emitting display according to an embodiment includes an organic light emitting panel 600 and a film 700 disposed on one surface of the organic light emitting panel 600.

The organic light emitting panel 600 may include a base substrate 610, a lower electrode 620, an organic emission layer 630, an upper electrode 640, and an encapsulation substrate 650.

The base substrate 610 may be made of glass or plastic.

One of the lower electrode 620 and the upper electrode 640 may be an anode, and the other one may be a cathode. The anode is an electrode to which holes are injected, and it may be made of a conducting material having a high work function. The cathode is an electrode to which electrons are injected, and it may be made of a conducting material having a low work function. At least one of the lower electrode 620 and the upper electrode 640 may be made of a transparent conductive material, for example ITO or IZO.

The organic emission layer 630 includes an organic material which may emit light when a voltage is applied to the lower electrode 620 and the upper electrode 640.

An auxiliary layer (not shown) may be further provided between the lower electrode 620 and the organic emission layer 630 and between the upper electrode 640 and the organic emission layer 630. The auxiliary layer is used to balance electrons and holes, and may include a hole transport layer, a hole injection layer (HIL), an electron injection layer (EIL), and an electron transporting layer, but is not limited thereto.

The encapsulation substrate 650 may be made of glass, a metal, or a polymer, and may seal the lower electrode 620, the organic emission layer 630, and the upper electrode 640 to prevent moisture and/or oxygen inflow from the outside.

The film 700 may be disposed on the side emitting light. For example, in the embodiment of a bottom emission structure emitting light at the side of the base substrate 610, the film may be disposed on the exterior side of the base substrate 610, while in the embodiment of a top emission structure emitting light at the side of the encapsulation substrate 650, the film may be disposed on the exterior side of the encapsulation substrate encapsulation substrate 650.

The film 700 may be the optical film 100, the compensation film 300, or the antireflective film 500. For example, when the film 700 is an antireflective film 500, light that inflows through the antireflective film 500 is prevented from being reflected by a reflection layer made of a metal such as an electrode and a wire of the organic light emitting panel 600, and is prevented from emitting to the external surface of the display device to improve display characteristics of the organic light emitting diode (OLED) display.

Hereinafter, a liquid crystal display (LCD) is described as an example of the display device.

Figure 7:
FIG. 7 is a schematic cross-sectional view of a liquid crystal display according to an embodiment.

FIG. 7 is a schematic cross-sectional view showing a liquid crystal display (LCD) device according to an embodiment.

Referring to FIG. 7, the liquid crystal display (LCD) according to an embodiment includes a liquid crystal panel 800, and a film 700 disposed on one surface of the liquid crystal panel 800.

The liquid crystal panel 800 may be a twist nematic (TN) mode panel, a homeotropic alignment (PVA) mode panel, an in-plane switching (IPS) mode panel, an optically compensated bend (OCB) mode panel, or the like.

The liquid crystal panel 800 may include a first display panel 810, a second display panel 820, and a liquid crystal layer 830 interposed between the first display panel 810 and the second display panel 820.

The first display panel 810 may include, for example, a thin film transistor (not shown) formed on a substrate (not shown) and a first electric field generating electrode (not shown) connected to the same, and the second display panel 820 may include, for example, a color filter (not shown) formed on a substrate (not shown) and a second electric field generating electrode (not shown). However, it is not limited thereto, and the color filter may be included in the first display panel 810, while the first electric field generating electrode and the second electric field generating electrode may be disposed on the first display panel 810 together therewith.

The liquid crystal layer 830 may include a plurality of liquid crystal molecules. The liquid crystal molecules may have positive or negative dielectric anisotropy. When the liquid crystal molecules have positive dielectric anisotropy, the major axes thereof may be aligned substantially parallel to the surface of the first display panel 810 and the second display panel 820 when an electric field is not applied, and the major axes may be aligned substantially perpendicular to the surface of the first display panel 810 and second display panel 820 when an electric field is applied. On the other hand, when the liquid crystal molecules have negative dielectric anisotropy, the major axes may be aligned substantially perpendicular to the surface of the first display panel 810 and the second display panel 820 when an electric field is not applied, and the major axes may be aligned substantially parallel to the surface of the first display panel 810 and the second display panel 820 when an electric field is not applied.

The film 700 may be the optical film 100, the compensation film 300, or the anti-reflective film 500. The film 700 is disposed on the outside of the liquid crystal panel 800. Although it is shown to be provided on both the lower part and the upper part of the liquid crystal panel 800 in the drawing, they are not limited thereto, and they may be formed on only one of the lower part and the upper part of the liquid crystal panel 800.

Hereinafter, the present disclosure is illustrated in more detail with reference to examples. However, these examples are exemplary, and the present disclosure is not limited thereto.

EXAMPLES

Synthesis Example 1: Preparation of Polymerizable Liquid Crystal Compound of Chemical Formula 1a 2,5-bis-[4-(3-acryloyloxy-propoxy)-benzoyloxy]-benzoic acid 4-(4-phenylethynyl-phenylethynyl)-benzyl ester represented by Chemical Formula 1a is synthesized according to the following process.

Synthesis Example 1a-1: Synthesis of 2,5-dihydroxy-benzoic Acid 4-bromobenzyl Ester Reaction Scheme 1a-1

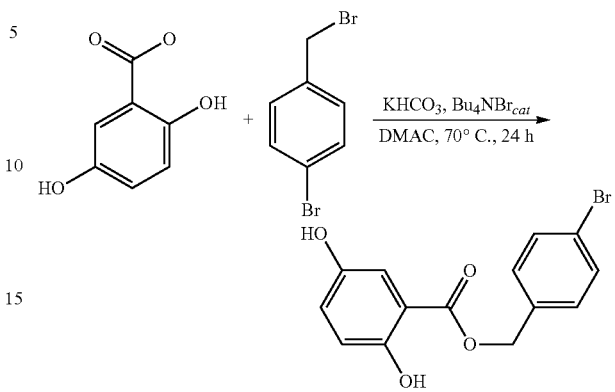

2,5-dihydroxybenzoic acid (mw=154.13 grams per mole (g/mol), 101 millimoles (mmol), m=15.57 grams (gr)), 1-bromo-4-bromomethylbenzene (mw=249.93 g/mol, 101 mmol, m=25.25 gr), potassium hydrogen carbonate (mw=100.12 g/mol, 303 mmol, m=30.35 gr), and tetrabutylammonium bromide (mw=322.37 g/mol, 3 mmol, m=0.97 gr) are added to 150 milliliters (mL) of dimethyl acetamide (DMAC), and the mixture is stirred for 24 hours under a nitrogen atmosphere. After the reaction is complete, the mixture is poured into 500 mL of water. The obtained precipitate is filtered, washed with water, suspended in 600 mL of water, and then stirred at 50° C. for 10 minutes. The mixture is cooled to room temperature (24° C.), a solid is filtered, and then dried at 80° C. for 24 hours under a reduced pressure. The product as a white solid (mw=323.15 g/mol, 99.4 mmol, m=32.13 gr) is obtained using a TLC silica gel (eluent:ethyl acetate:hexane=1:4 volume ratio). The yield of the product is 98.4%.

$^1$H NMR (DMSO-$d_6$) 300 MHz, δ, ppm: 5.33 (s, 2H), 6.83 (d, 1H, $J^{12}$=9 Hz), 6.98 (dd, 1H, $J^{12}$=9 Hz, $J^{13}$=3.0 Hz), Chemical Formula 1a

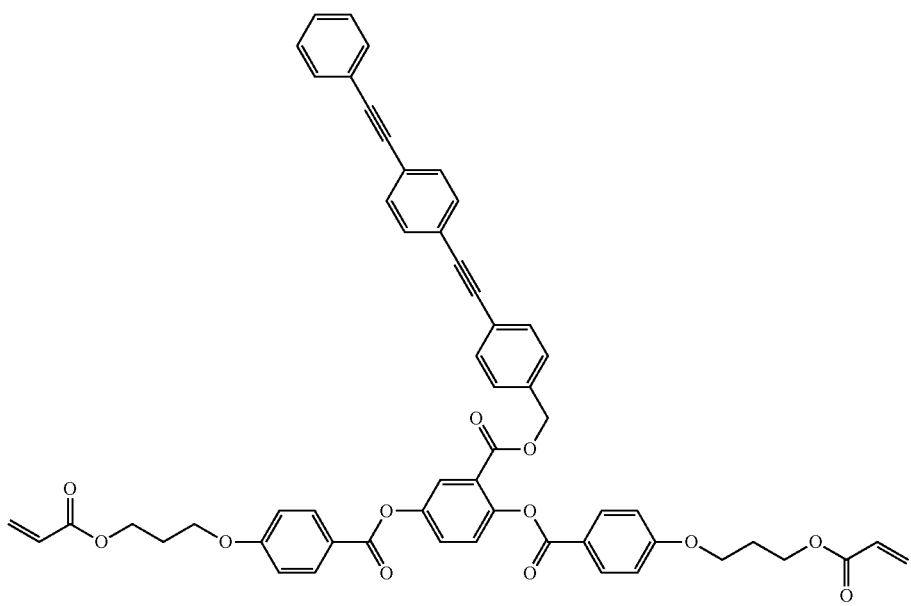

7.17 (d, 1H, $J^{13}$=3.0 Hz), 7.45 (d, 2H, $J^{12}$=8.4 Hz), 7.62 (d, 2H, $J^{12}$=8.4 Hz), 9.20 (s, 1H, OH), 9.89 (s, 1H, OH).

Synthesis Example 1a-2: Synthesis of 2,5-dihydroxybenzoic Acid 4-(4-phenylethynyl-phenylethynyl)benzyl Ester Reaction Scheme 1a-2

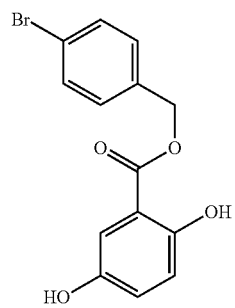

+

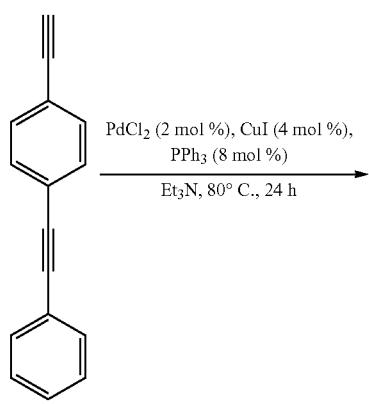

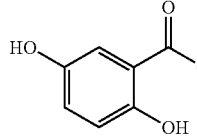

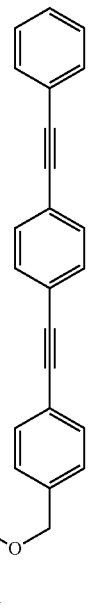

2,5-dihydroxy-benzoic acid 4-bromobenzyl ester (mw=323.15 g/mol, 99 mmol, m=32 gr) and 1-ethynyl-4-phenylethynylbenzene (mw=202.26 g/mol, 102 mmol, m=20.63 gr) are dissolved in 0.5 liters (L) of $Et_3N$ in a 1 L three-necked round bottom flask equipped with a nitrogen inlet and a condenser. The obtained solution is stirred and purged with dry nitrogen gas for 1 hour. Palladium (II) chloride (mw=177.33 g/mol, 2 mmol, m=0.35 gr), copper (I) iodide (mw=190.45 g/mol, 4 mol, m=0.76 gr), and triphenylphosphine (mw=262.45 g/mol, 8 mol, m=2.1 gr) are added to the stirred solution. A nitrogen flow is kept for additional 10 minutes, and then, a nitrogen outlet is closed, and the mixture is kept stirred under the nitrogen at 80° C. for 24 hours. After the reaction is complete, $Et_3N$ is evaporated under a reduced pressure to obtain the crude product as a brown solid. The product is suspended in 400 mL of iso-propanol and heated for 30 minutes to obtain a brown precipitate. The obtained brown precipitate is added to 400 mL of methanol and then, boiled for 30 minutes to obtain a light-brown precipitate. The light-brown precipitate is added to 400 mL of methanol and boiled for 30 minutes to obtain a light-brown precipitate. The purified product is vacuum-dried at 75° C. for 24 hours.

A light-brown powder (mw=444.49 g/mol, 72.2 mmol, m=32.1 gr) is obtained using a TLC silica gel (eluent:ethyl acetate:hexane=1:2 volume ratio). The yield is 73%.

$^1$H NMR (DMSO-$d_6$) 300 MHz, δ, ppm: 5.41 (s, 2H), 6.82 (d, 1H, $J^{12}$=9 Hz), 6.97 (dd, 1H, $J^{12}$=9 Hz, $J^{13}$=3.0 Hz), 7.20 (d, 1H, $J^{13}$=3.0 Hz), 7.44-7.46 (m, 3H), 7.53-7.65 (m, 10H), 9.23 (s, 1H, OH), 9.91 (s, 1H, OH).

Synthesis Example 1a-3: Synthesis of 2,5-bis-[4-(3-acryloyloxypropoxy)benzoyloxy]benzoic Acid 4-(4-phenylethynylphenylethynyl)benzyl Ester
Reacton Scheme 1a-3
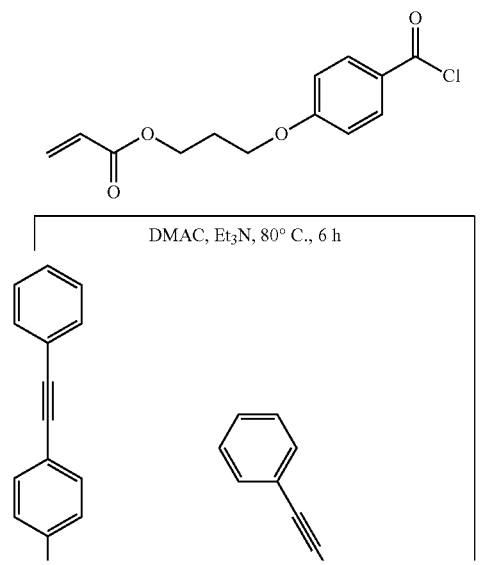
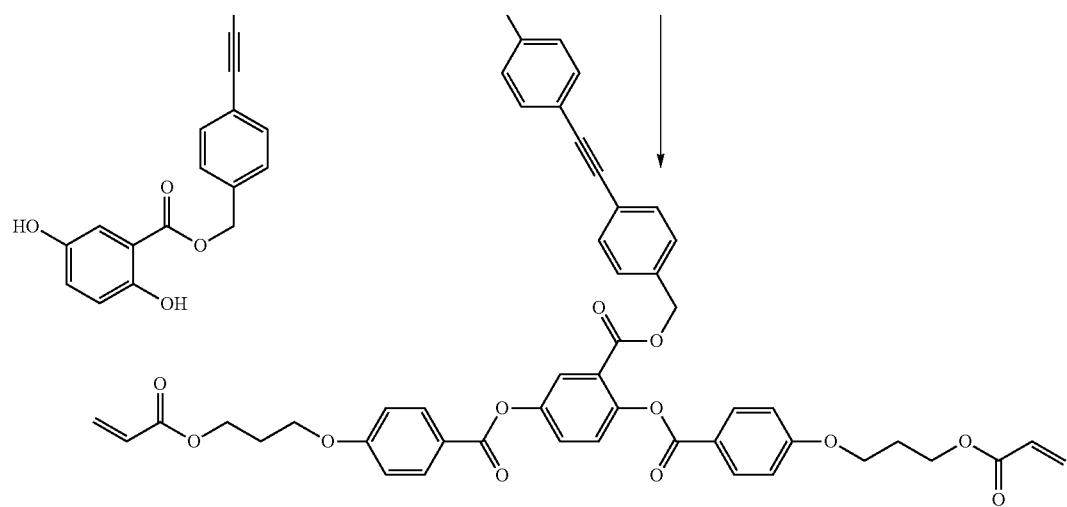

The 2,5-dihydroxybenzoic acid 4-(4-phenylethynyl-phenylethynyl)benzyl ester (mw=444.49 g/mol, 22.5 mmol, Chemical Formula 1b

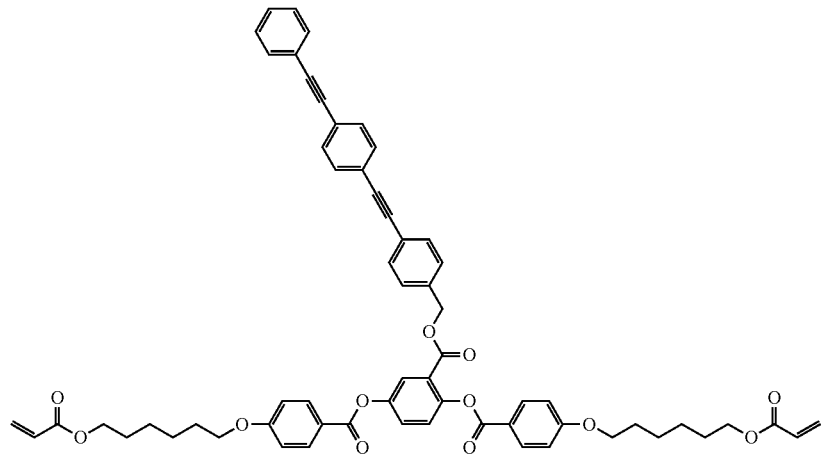

m=10 gr) of Synthesis Example 1a-2 is dissolved in 150 mL of dimethyl acetamide (DMAC) to obtain a first solution. A second solution including acrylic acid 3-(4-chlorocarbonyl-phenoxy)propyl ester (mw=268.7 g/mol, 67.5 mmol, m=18.1 gr) dissolved in 50 mL of DMAC is added to the first solution while stirred. Then, triethylamine (mw=101 g/mol, 90 mmol, m=9.1 gr) is added thereto, and the resulting mixture is stirred under a nitrogen gas atmosphere at 80° C. for 6 hours. After the reaction is complete, the dark-brown solution is poured into 2 L of water and extracted with 500 mL of EtOAc three times. The obtained organic material extract is washed with water, the solvent is evaporated, the resultant is purified using about 2 L of dichloromethane (DCM) as an eluent to remove a yellow colored byproduct, and a major fraction of the product is separated using an eluent of ethyl acetate and hexane (ethyl acetate:hexane=1:3 volume ratio) and is purified using silica gel flash chromatography to obtain a brown material. The solvent is evaporated to obtain an off-white product which is crystallized from a mixture of dichloromethane and methanol by careful azeotropic substitution of dichloromethane for methanol. The obtained precipitate is filtered, washed with methanol, and dried at 50° C. for 24 hours. The product is a slightly off-white crystalline solid (mw=908.97 g/mol, 13.1 mmol, m=11.9 gr), and the yield is 58%.

$^1$H NMR (DMSO-ds) 300 MHz, δ, ppm: 2.09-2.15 (m, 4H), 4.17-4.32 (m, 8H), 5.22 (s, 2H), 5.93-5.98 (m, 2H), 6.14-6.24 (m, 2H), 6.31-6.33 (m, 1H), 6.37-6.38 (m, 1H), 7.06 (d, 2H, $J^{12}$=9 Hz), 7.15 (d, 2H, $J^{12}$=9 Hz), 7.31 (d, 2H, $J^{12}$=8.4 Hz), 7.41-7.50 (m, 6H), 7.57-7.61 (m, 6H), 7.68 (dd, 1H, $J^{12}$=8.4 Hz, $J^{13}$=3.0 Hz), 7.91 (d, 1H, $J^{13}$=3.0 Hz), 7.96 (d, 2H, $J^{12}$=9.0 Hz), 8.11 (d, 2H, $J^{12}$=9.0 Hz).

Synthesis Example 2: Preparation of Polymerizable Liquid Crystal Compound of Chemical Formula 1b 2,5-bis-[4-(3-acryloyloxy-hexyloxy)-benzoyloxy]-benzoic acid 4-(4-phenylethynyl-phenylethynyl)-benzyl ester represented by Chemical Formula 1b is synthesized according to the following process.

A crystalline solid is obtained according to the same method as in Synthesis Example 1, except that acrylic acid 3-(4-chlorocarbonylphenoxy)hexyl ester (mw=292.33 g/mol) is used instead of the acrylic acid 6-(4-chlorocarbonylphenoxy)propyl ester of Synthesis Example 1a-3 in Synthesis Example 1.

Synthesis Example 3: Preparation of Polymerizable Liquid Crystal Compound of Chemical Formula 1c 2,5-bis-[4-(3-acryloyloxy-propoxy)-benzoyloxy]-benzoic acid 4-(4-phenylethynyl-phenylethynyl)benzyl-amide represented by Chemical Formula 1c is synthesized according to the following process.

Chemical Formula 1c

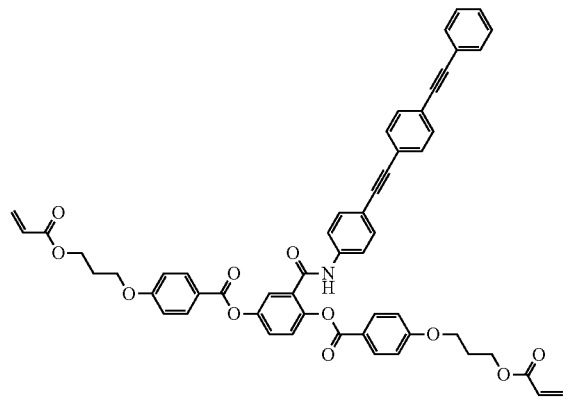

Synthesis Example 1c-1: Synthesis of 2,5-diacetoxybenzoic Acid

Reaction Scheme 1c-1

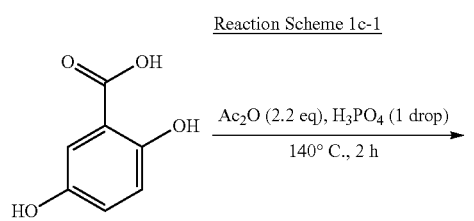

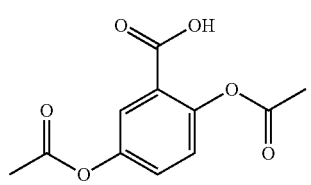

2,5-dihydroxybenzoic acid (mw=154.13 g/mol, 324.4 mmol, m=50 gr), acetic anhydride (mw=102.1 g/mol, 713.7 mmol, m=72.9 gr), and 1 drop of phosphoric acid are stirred at 140° C. for 2 hours while heating the resultant. The mixture is cooled to room temperature and poured into 700 mL of iced water while stirred. The obtained white precipitate is filtered, washed with water, and then dried at 60° C. for 24 hours under a reduced pressure.

A white solid, 2,5-diacetoxybenzoic acid (mw=238.2 g/mol, 276.4 mmol, m=65.8 gr) is obtained. The yield is 85.2%.

Synthesis Example 1c-2: Synthesis of Acetic Acid 3-(4-bromophenylcarbamoyl)-4-hydroxyphenyl Ester

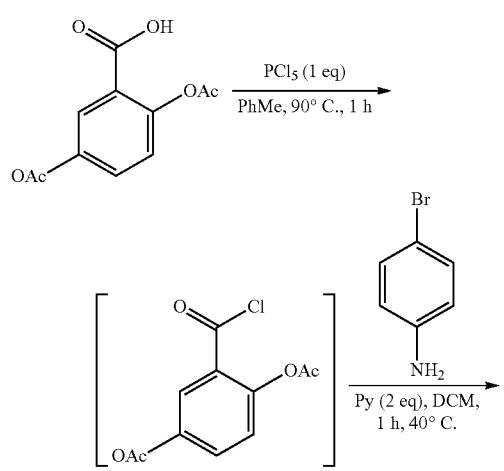

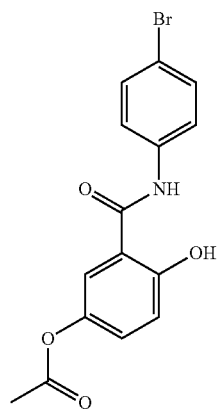

The 2,5-diacetoxybenzoic acid (mw=238.2 g/mol, 275.8 mmol, m=65.7 gr) of Synthesis Example 1c-1, phosphorous pentachloride (mw=208.2 g/mol, 275.8 mmol, m=57.4 gr), and 1 drop of pyridine are heated and then, stirred at 90° C. for 1 hour in 1 L of anhydrous toluene. Toluene and phosphorous oxychloride formed during the reaction are evaporated under a reduced pressure, and the obtained residue is dissolved in 1 L of dichloromethane while stirring the resultant. 4-bromoaniline (mw=172 g/mol, 275.8 mmol, m=47.4 gr) and pyridine (mw=79.1 g/mol, 551.6 mmol, m=43.6 gr) are carefully added to the stirred solution in this order. The mixture is refluxed at 40° C. for 1 hour, and the solvent is evaporated to crystallize the residue in 50% aqueous iso-propanol. The crude product containing a small amount of a by-product is crystallized from a small amount of methanol and dried to obtain acetic acid 3-(4-bromophenylcarbamoyl)-4-hydroxyphenyl ester (mw=350.2 g/mol, 142.8 mmol, m=50 gr, the yield: 51.8%) as a white crystalline solid.

$^1$H NMR (DMSO-$d_6$) 300 MHz, δ, ppm: 2.27 (s, 3H, C(O)CH$_3$), 7.02 (d, 1H, J$^{12}$=9.0 Hz), 7.22 (dd, 1H, J$^{12}$=9.0 Hz, J$^{13}$=3.0 Hz), 7.55 (d, 2H, J$^{12}$=9.0 Hz), 7.54 (d, 1H, J$^{13}$=3.0 Hz), 7.69 (d, 2H, J$^{12}$=9.0 Hz), 10.46 (s, 1H, NH), 10.94 (s, 1H, OH).

Synthesis Example 1c-3: Synthesis of N-(4-bromophenyl)-2,5-dihydroxybenzamide Reaction Scheme 1c-3

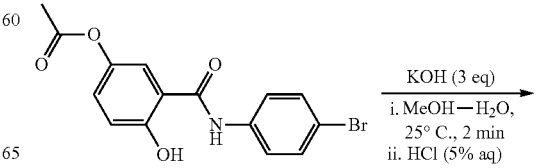

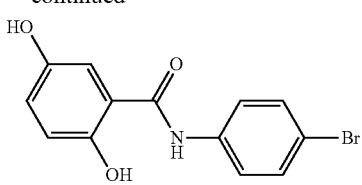

Acetic acid 3-(4-bromophenylcarbamoyl)-4-hydroxyphenyl ester (mw=350.2 g/mol, 142.8 mmol, m=50 gr) of Reaction Scheme 1c-2 is suspended in 0.5 L of methanol while stirring the resultant. Then, the solution of potassium hydroxide (mw=56 g/mol, 428.4 mmol, m=24 gr) in 50 mL of water is added to the suspension at room temperature. A clear brownish solution formed therein is stirred in 2 L of water for 2 minutes, and 5% aqueous hydrochloric acid is added thereto to adjust pH of the solution into acid. A slightly light-pink precipitate formed therein is filtered and dried under a reduced pressure at 60° C. for 24 hours. N-(4-bromophenyl)-2,5-dihydroxybenzamide of a light-pink powder (mw=308.1 g/mol, 138.5 mmol, m=42.7 gr) is obtained. The yield of the product is 97%.

$^1$H NMR (DMSO-$d_6$) 300 MHz, δ, ppm: 6.82 (d, 1H, $J^{12}$=8.7 Hz), 6.88 (dd, 1H, $J^{12}$=8.7 Hz, $J^{13}$=3.0 Hz), 7.32 (dd, 1H, $J^{13}$=3.0 Hz), 7.54 (d, 2H, $J^{12}$=8.7 Hz), 7.69 (d, 2H, $J^{12}$=8.7 Hz), 9.12 (s, 1H, OH), 10.46 (s, 1H, NH), 10.92 (s, 1H, OH).

Synthesis Example 1c-4: Synthesis of 2,5-dihydroxy-N-[4-(4-phenylethynyl-phenylethynyl)phenyl]-benzamide Reaction Scheme 1c-4

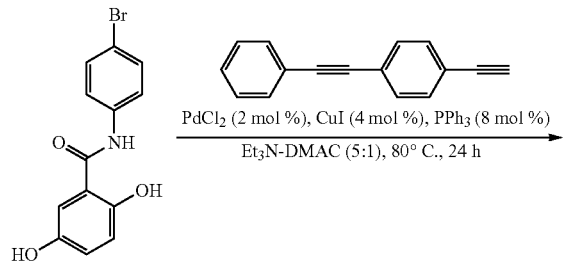

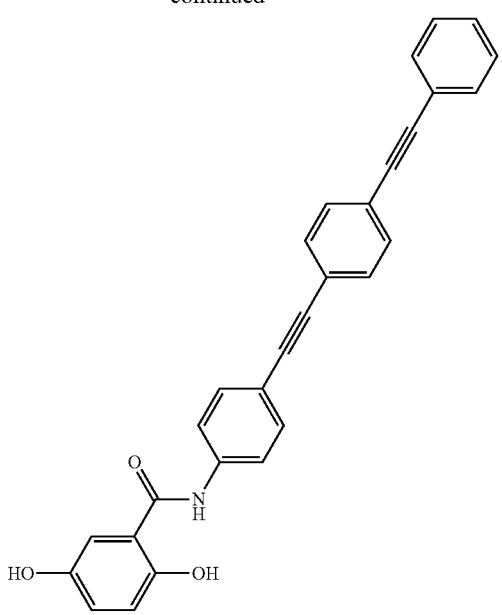

N-(4-bromophenyl)-2,5-dihydroxybenzamide (mw=308.1 g/mol, 69.1 mmol, m=20 gr) and 1-ethynyl-4-phenylethynylbenzene (mw=308.1 g/mol, 69.1 mmol, m=20 gr) are dissolved in a mixture of 0.5 L of Et$_3$N and 0.1 L of DMAC in a 1 L two-necked round bottom flask equipped with a nitrogen inlet and a condenser. The resulting solution is purged with dry nitrogen gas for 1 hour. Palladium (II) chloride (mw=177.33 g/mol, 1.3 mmol, m=0.23 gr), copper (I) iodide (mw=190.45 g/mol, 2.6 mmol, m=0.5 gr) and triphenylphosphine (mw=262.45 g/mol, 5.2 mmol, m=1.37 gr) are added to the stirred solution. A nitrogen flow is kept for additional 10 minutes, and then, a nitrogen outlet is closed, and the mixture is kept stirred under nitrogen at 80° C. for 24 hours. After the reaction is complete, the solvent is evaporated under a reduced pressure, and the residue is suspended in 300 mL of boiling iso-propanol and then, filtered when cooled. The resulting brown solid is stirred in 150 mL of boiling ethyl acetate and filtered after being cooled. This operation is performed 3 times until mother liquor becomes light yellow. The filtered product is dried at 60° C. for 24 hour to obtain 2,5-dihydroxy-N-[4-(4-phenylethynyl-phenylethynyl)phenyl]-benzamide (mw=429.48 g/mol, 25.1 mmol, m=10.8 gr) as a heavy dark-brown powder. The yield of the product is 36.3%.

$^1$H NMR (DMSO-$d_6$) 300 MHz, δ, ppm: 6.83 (d, 1H, $J^{12}$=8.7 Hz), 6.88 (dd, 1H, $J^{12}$=8.7 Hz, $J^{13}$=3.0 Hz), 7.35 (dd, 1H, $J^{13}$=3.0 Hz), 7.45-7.60 (m, 12H), 7.81 (d, 2H, $J^{12}$=8.4 Hz), 9.15 (s, 1H, OH), 10.58 (s, 1H, NH), 10.89 (s, 1H, OH).

Synthesis Example 1c-5: Synthesis of 2,5-bis-[4-(3-acryloyloxypropoxy)benzoyloxy]-N-[4-(4-phenyl-ethynyl-phenylethynyl)phenyl]benzamide

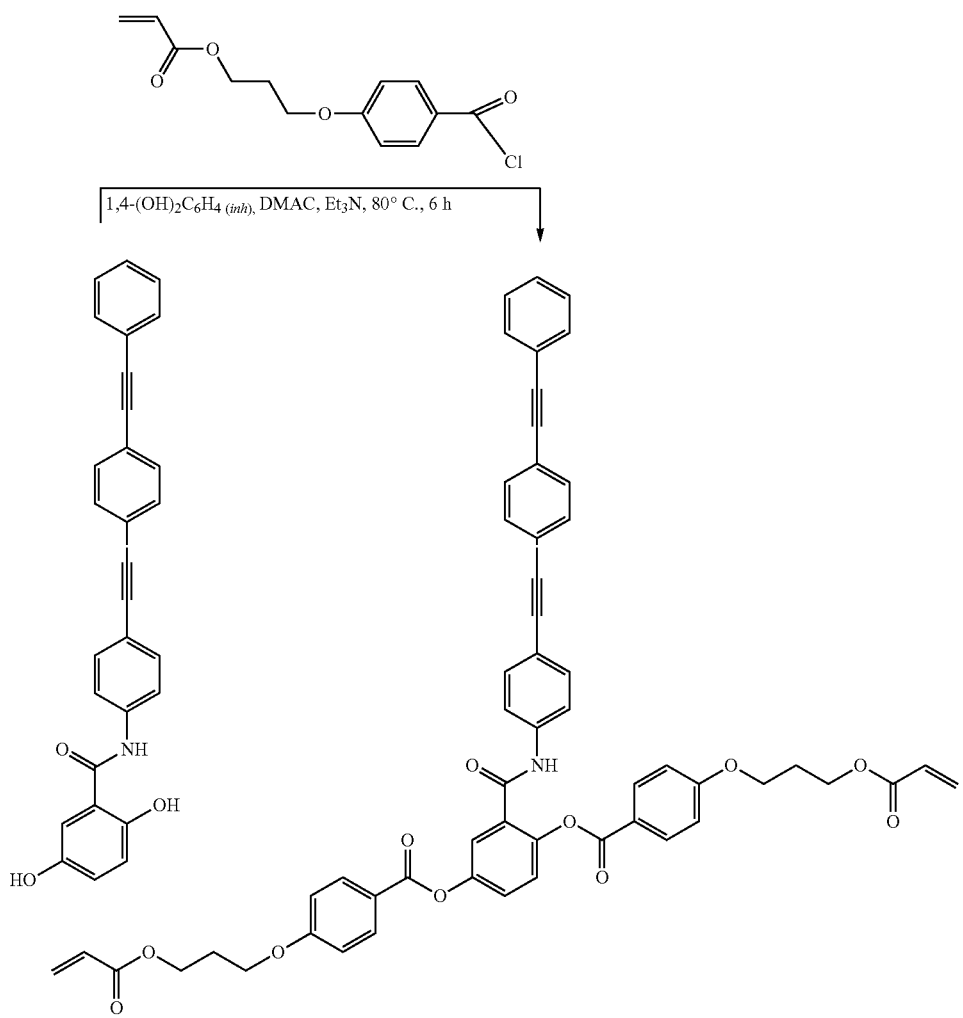

Reaction Scheme 1c-5

The 2,5-dihydroxy-N-[4-(4-phenylethynyl-phenylethynyl)phenyl]-benzamide (mw=429.48 g/mol, 23.3 mmol, m=10 gr) of Synthesis Example 1c-4 and 10 mg of hydroquinone (acrylate polymerization inhibitor) are dissolved in 150 mL of dimethyl acetamide (DMAC) to obtain a first solution. A second solution including acrylic acid 3-(4-chlorocarbonylphenoxy)propyl ester (mw=268.7 g/mol, 69.9 mmol, m=17.5 gr) dissolved in 50 mL of DMAC is added to the first solution while stirring the resultant. Then, triethylamine (mw=101 g/mol, 95.2 mmol, m=9.4 gr) is added thereto, and the resulting mixture is stirred under a nitrogen gas atmosphere at 80° C. for 6 hours. After the reaction is complete, the dark-brown solution is poured into 1 L of cold water, and the resulting suspension is stirred for 2 hours. Then, solids are filtered, washed with water, suspended in 400 mL of hot methanol and filtered to remove an excess of non-reacted acid. The filtered solids are dissolved in 800 mL of a boiling mixed solvent of methanol-dichloromethane (1:1 volume ratio), treated with decolorizing charcoal, and filtered. The solution after the filtration is concentrated by refluxing to substitute dichloromethane for methanol, and thereby solid materials are precipitated. The solids are filtered, washed with methanol, and dried under a reduced pressure at 60° C. for 24 hours. The product as a light beige powder (mw=894 g/mol, 18.3 mmol, m=16.4 gr) is obtained using a TLC silica gel (eluent ethyl acetate:hexane=1:1 volume ratio). The yield of the product is 78.5%

$^1$H NMR (DMSO-$d_6$) 300 MHz, δ, ppm: 2.09-2.15 (m, 4H), 4.16-4.32 (m, 8H), 5.93-5.98 (m, 2H), 6.14-6.24 (m, 2H), 6.31-6.38 (m, 2H), 7.07 (d, 2H, $J^{12}$=9 Hz), 7.16 (d, 2H, $J^{12}$=9 Hz), 7.44-7.72 (m, 16H), 8.05 (d, 2H, $J^{12}$=9 Hz), 8.12 (d, 2H, $J^{12}$=9.0 Hz), 10.70 (s, 1H).

Synthesis Example 4: Preparation of Polymerizable Liquid Crystal Compound of Chemical Formula 1d 2,5-bis-[4-(6-acryloyloxy-hexyloxy)-benzoyloxy]-benzoic acid 4-(4-phenylethynyl-phenylethynyl)benzamide) of Chemical Formula 1d is synthesized according to the following process.

Chemical Formula 1d

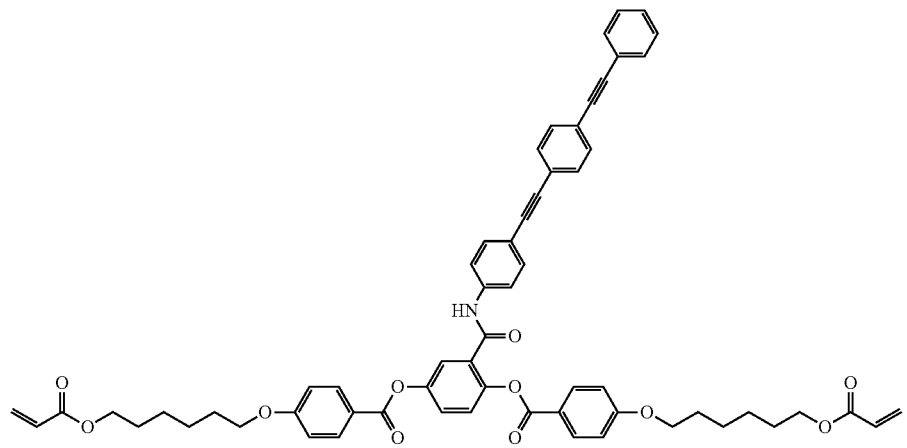

Synthesis Example 1d-1: Synthesis of 2,5-diacetoxy-N-(4-iodophenyl)benzamide and 5-acetoxy-2-hydroxy-N-(4-iodophenyl)benzamide Reaction Scheme 1d-1

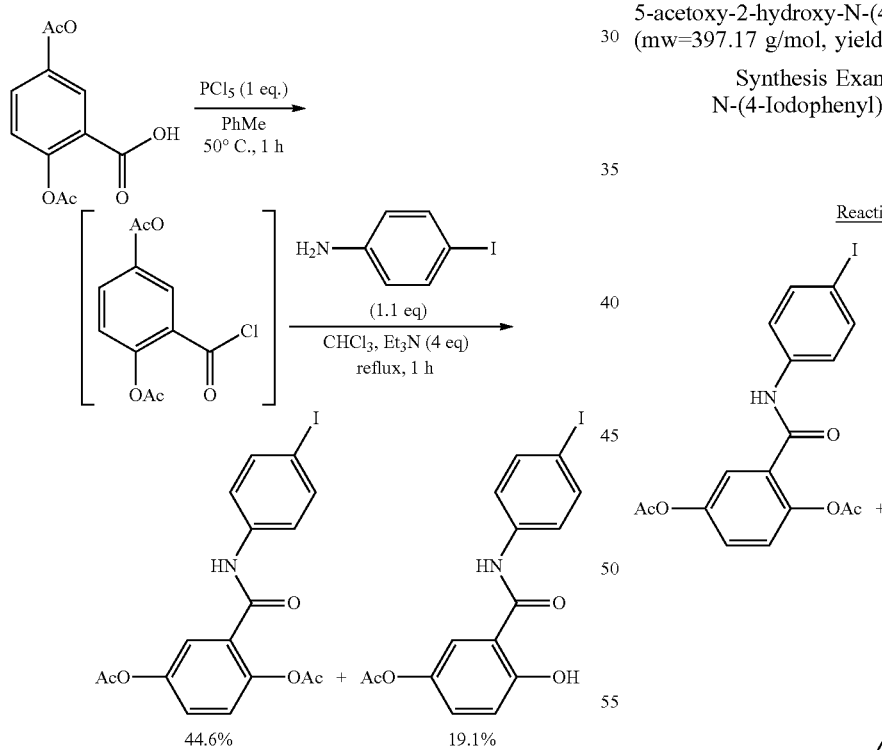

2,5-diacetoxybenzoic acid (mw=238.2 g/mol, 0.3 mmol, m=71.46 gr), phosphorus pentachloride (mw=208.2 g/mol, 0.3 mmol, m=62.47 gr), and 1 drop of pyridine are heated and stirred in 0.5 L of anhydrous toluene for 1 hour at 50° C. The obtained crude product of toluene and phosphorous oxychloride is distilled under a reduced pressure (5 millimeters of mercury (mmHg), bath temperature of 60° C.). The residue is dissolved in 0.5 L of chloroform to obtain a first solution. 4-iodoaniline (mw=219 g/mol, 0.33 mmol, m=72.3 gr) and triethylamine (mw=101 g/mol, 0.6 mmol, m=60.6 gr) are sequentially added to the first solution. The obtained mixture is refluxed for 1 hour to evaporate a solvent, and the residue is crystallized with iso-propanol (V=0.5 L). After drying the resultant, a mixture of 80.5 g of a white crystalline material, 2,5-diacetoxy-N-(4-iodophenyl)benzamide (mw=439.21 g/mol, the yield: 44.6%), and 5-acetoxy-2-hydroxy-N-(4-iodophenyl)benzamide (mw=397.17 g/mol, yield: 19.1%) is obtained.

Synthesis Example 1d-2: Synthesis of N-(4-Iodophenyl)-2,5-dihydroxybenzamide

Reaction Scheme 1d-2

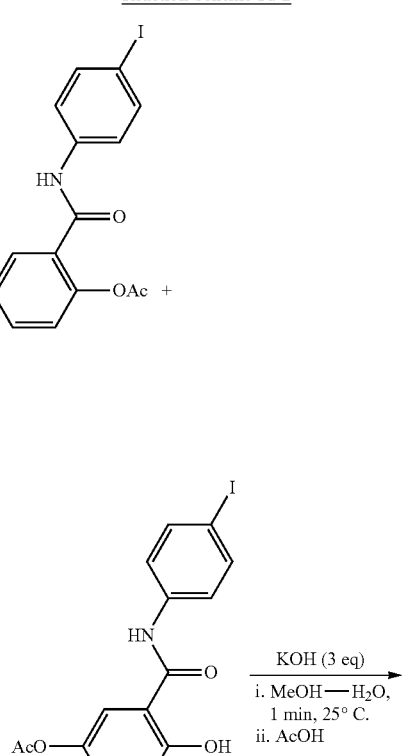

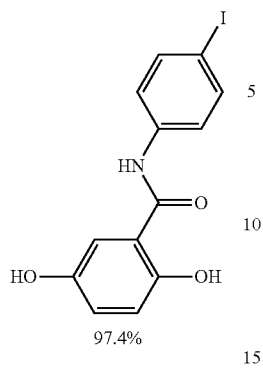

97.4%

A mixture (m=80.5 gr) of 2,5-diacetoxy-N-(4-iodophenyl)benzamide and 5-acetoxy-2-hydroxy-N-(4-iodophenyl) benzamide of Synthesis Example 1d-1 in a weight ratio of 7:3 is stirred and suspended in 0.5 L of methanol. A solution of potassium hydroxide (mw=56 g/mol, 573 mmol, m=32 gr) in 40 mL of water is added to the suspension at room temperature to obtain a brownish solution. The solution is treated with decolorizing charcoal and filtered. 2 L of water and 60 mL of acetic acid are added to the resultant to obtain a light-pink precipitate. The light-pink precipitate is filtered and dried under a reduced pressure at 60° C. for 24 hours to obtain N-(4-iodophenyl)-2,5-dihydroxybenzamide as a light-pink powder (mw=355.13 g/mol, 186 mmol, m=66 gr). The yield of the product is 97.4%

$^1$H NMR (DMSO-d$_6$) 300 MHz, δ, ppm: 6.82 (d, 1H, J$^{12}$=8.7 Hz), 6.88 (dd, 1H, J$^{12}$=8.7 Hz, J$^{13}$=3.0 Hz), 7.32 (dd, 1H, J$^{13}$=3.0 Hz), 7.55 (d, 2H, J$^{12}$=9 Hz), 7.69 (d, 2H, J$^{12}$=9 Hz), 9.12 (s, 1H, OH), 10.44 (s, 1H, NH), 10.93 (s, 1H, OH).

Synthesis Example 1d-3: Synthesis of 2,5-dihydroxy-N-[4-(4-phenylethynyl-phenylethynyl)phenyl]-benzamide Reaction Scheme 1d-3

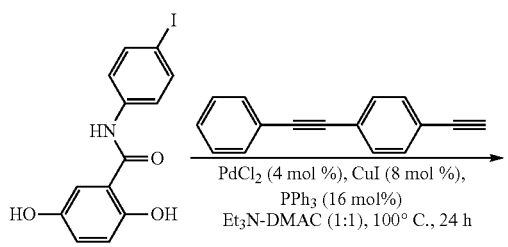

PdCl$_2$ (4 mol %), CuI (8 mol %), PPh$_3$ (16 mol%)
Et$_3$N-DMAC (1:1), 100° C., 24 h

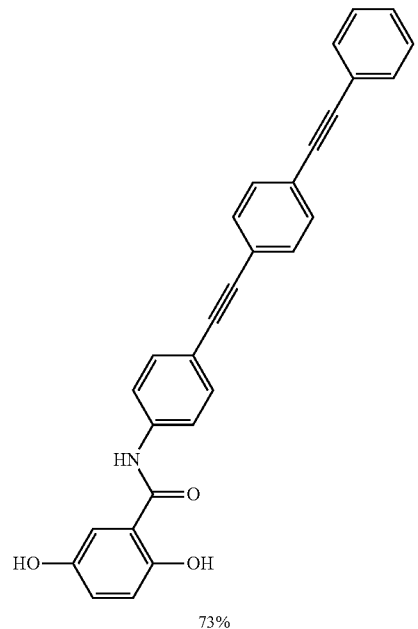

73%

N-(4-iodophenyl)-2,5-dihydroxybenzamide (mw=355.13 g/mol, 0.1 mol, m=35.5 gr) and 1-ethynyl-4-phenylethynyl-benzene (mw=202.26 g/mol, 0.1 mol, m=20.2 gr) are dissolved in a mixture of 0.3 L of Et$_3$N and 0.3 L of DMAC in a 1 L two-necked round bottom flask equipped with a nitrogen inlet and a condenser. The resulting solution is purged with a dry nitrogen gas for 1 hour. Then, palladium (II) chloride (mw=177.33 g/mol, 4 mmol, m=0.71 gr), copper (I) iodide (mw=190.45 g/mol, 8 mmol, m=1.52 gr) and triphenylphosphine (mw=262.45 g/mol, 16 mmol, m=4.2 gr) are added to the stirred solution. A nitrogen flow is kept for additional 10 minutes, and then, a nitrogen outlet is closed, and the mixture is kept stirred under nitrogen for 24 hours at 100° C. After completion of the reaction, the solvent is evaporated under a reduced pressure, and the residue is suspended in 500 mL of boiling iso-propanol and filtered on cooling. The resulting brown solid is stirred in 300 mL of boiling ethyl acetate and filtered after cooling. This operation is done 3 times until the color of the solution becomes light yellow. The solid after the filtration is dried at 60° C. for 24 hours to obtain 2,5-dihydroxy-N-[4-(4-phenylethynylphenylethynyl)phenyl]benzamide as a heavy dark-brown powder (mw=429.48 g/mol, 72.9 mmol, m=31.3 gr). The yield of the product is 73%.

$^1$H NMR (DMSO-d$_6$) 300 MHz, δ, ppm: 6.83 (d, 1H, J$^{12}$=8.7 Hz), 6.88 (dd, 1H, J$^{12}$=8.7 Hz, J$^{13}$=3.0 Hz), 7.35 (dd, 1H, J$^{13}$=3.0 Hz), 7.45-7.60 (m, 12H), 7.81 (d, 2H, J$^{12}$=8.4 Hz), 9.15 (s, 1H, OH), 10.58 (s, 1H, NH), 10.89 (s, 1H, OH).

Synthesis Example 1d-4: Synthesis of 2,5-bis-[4-(6-acryloyloxyhexyloxy)benzoyloxy]-N-[4-(4-phenyl-ethynylphenylethynyl)phenyl]benzamide Reaction Scheme 1d-4

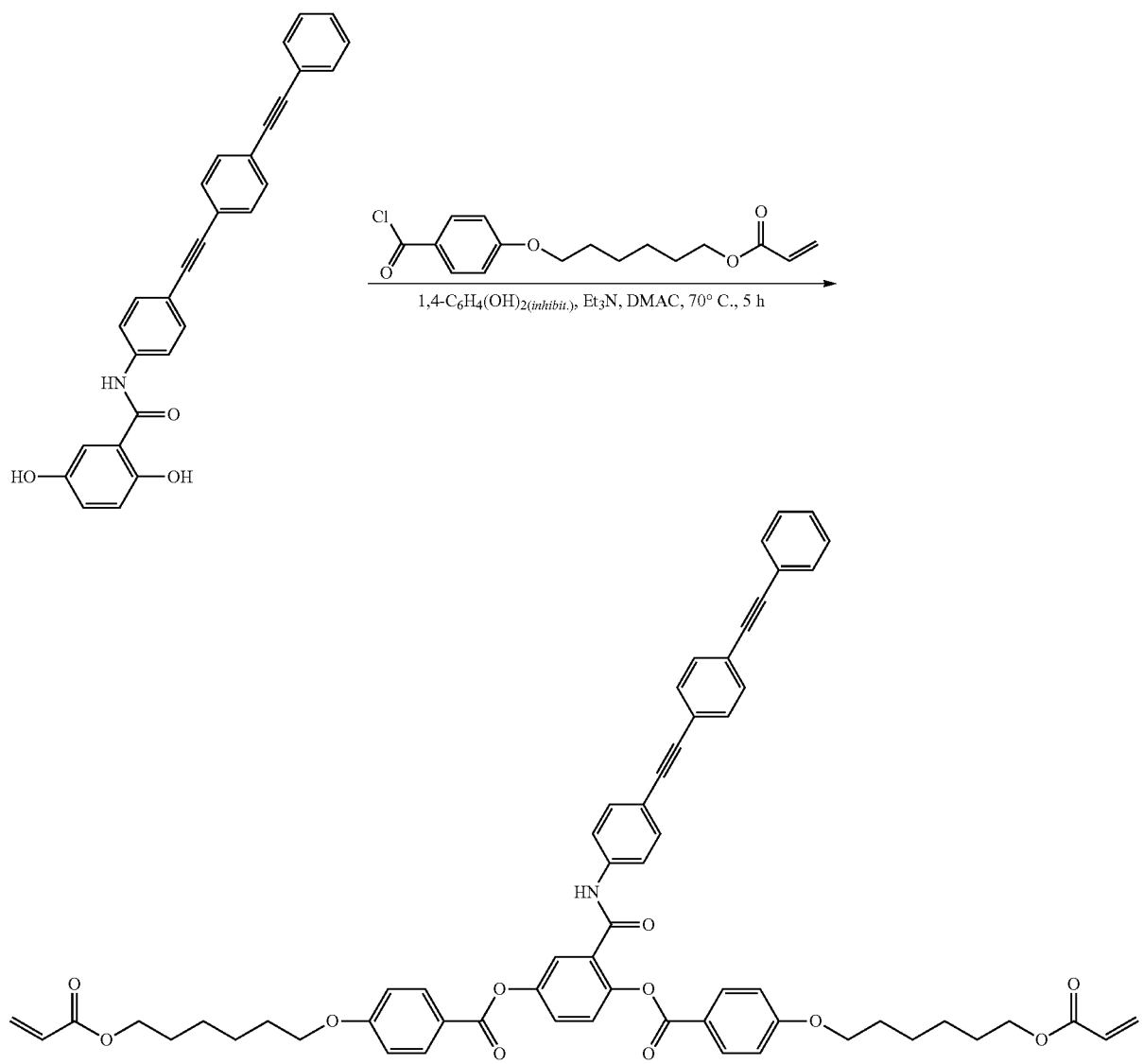

2,5-dihydroxy-N-[4-(4-phenylethynyl-phenylethynyl)phenyl]-benzamide (mw=429.48 g/mol, 34.93 mmol, m=15 gr) and 10 mg of hydroquinone (acrylate polymerization inhibitor) are dissolved in 100 mL of dimethylacetamide (DMAC) to obtain a first solution, and a second solution of acrylic acid 6-(4-chlorocarbonylphenoxy)hexyl ester (mw=310.78 g/mol, 94.31 mmol, m=29.3 gr) in 100 mL of DMAC is added to the first solution while stirring the resultant. Then, triethylamine (mw=101 g/mol, 139.7 mmol, m=14.1 gr) is added thereto, and the resulting mixture is stirred for 5 hours at 70° C. under a nitrogen gas atmosphere. After a reaction is complete, the dark-brown solution is poured into 1 L of cold water, and the resulting suspension is stirred for 1 hour. A solid is filtered, washed with water (V=500 mL) and methanol (V=500 mL), then suspended in 500 mL of hot methanol, and filtered to remove an excess of a non-reacted acid. A light-brown solid after filtration is dissolved in 800 mL of a boiling mixed solvent of methanol and dichloromethane (1:1 volume ratio), treated with decolorizing charcoal, and filtered. The filtered solution is concentrated using a rotary evaporator to obtain a solid precipitate material. The solid precipitate material is filtered, washed with methanol, and dried under a reduced pressure at 60° C. for 24 hours. A light beige powder (mw=978.12 g/mol, 30.5 mmol, m=29.8 gr, the yield: 87.3%) is obtained using a TLC silica gel (eluent:ethyl acetate:hexane=1:2 volume ratio).

$^1$H NMR (DMSO-$d_6$) 300 MHz, δ, ppm: 1.33-1.53 (m, 8H), 1.58-1.82 (m, 8H), 1.58-1.82 (m, 8H), 4.05-4.15 (m, 8H), 5.90-5.96 (m, 2H), 6.13-6.22 (m, 2H), 6.28-6.31 (m, 2H), 7.06 (d, 2H, $J^{12}$=9 Hz), 7.14 (d, 2H, $J^{12}$=9 Hz), 7.43-7.59 (m, 13H), 7.67-7.73 (m, 3H), 8.05 (d, 2H, $J^{12}$=9 Hz), 8.11 (d, 2H, $J^{12}$=9.0 Hz), 10.71 (s, 1H).

Synthesis Example 5: Preparation of Polymerizable Liquid Crystal Compound of Chemical Formula 1e Chemical Formula 1e

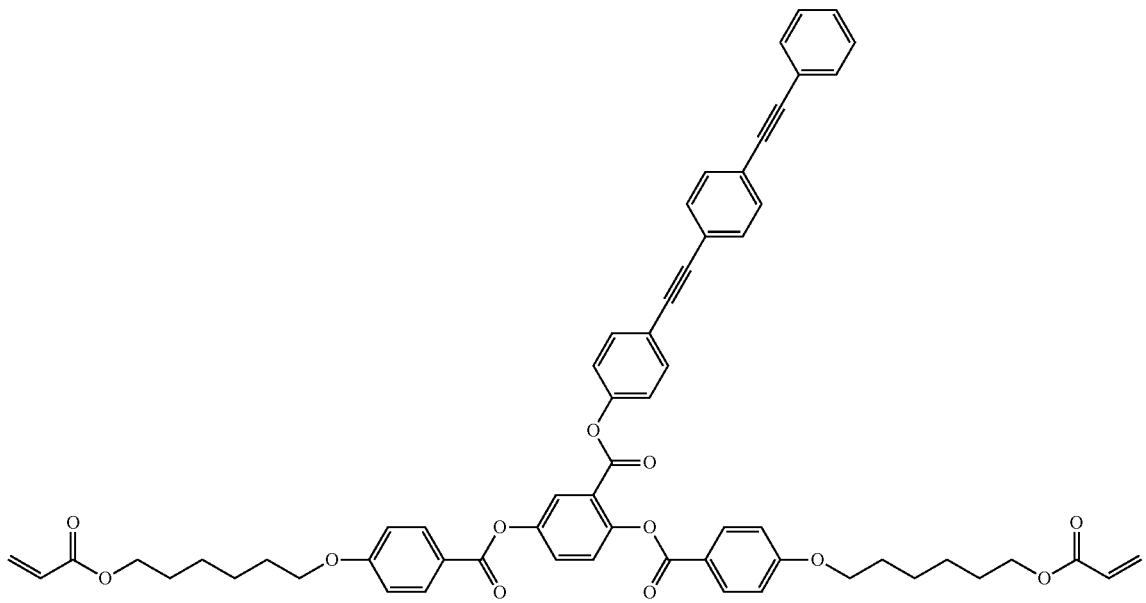

Synthesis Example 1e-1: Synthesis of 2,5-Diacetoxybenzoic Acid 4-iodophenyl Ester Reaction Scheme 1e-1

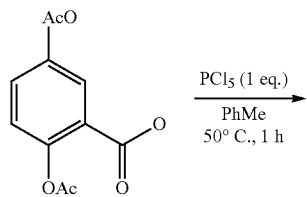

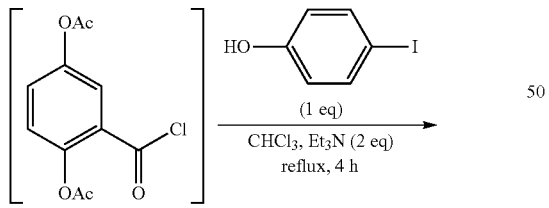

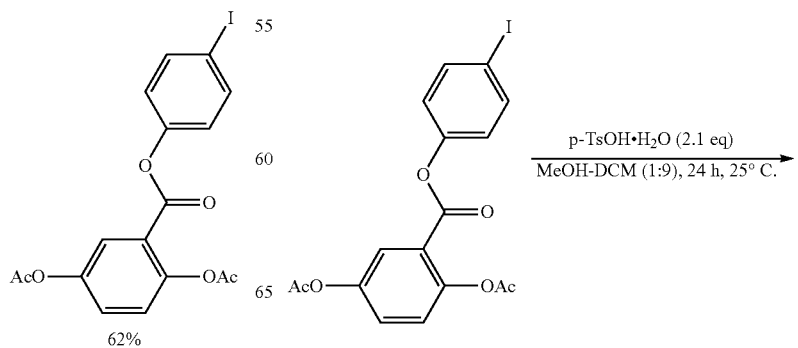

2,5-diacetoxybenzoic acid (mw=238.2 g/mol, 0.342 mol, m=81.6 gr), phosphorus pentachloride (mw=208.2 g/mol, 0.342 mol, m=71.3 gr), and 1 drop of pyridine are heated and stirred in 0.5 L of anhydrous toluene for 1 hour at 50° C. Toluene and phosphorous oxychloride generated during the reaction are evaporated under a reduced pressure (5 mmHg, bath temperature of 60° C.). The resulting residue is dissolved while stirred in 0.5 L of $CHCl_3$. 4-iodophenol (mw=220 g/mol, 0.342 mol, m=75.3 gr) and triethylamine (mw=101 g/mol, 0.69 mol, m=69.7 gr) are carefully added to the solution in this order. The mixture is refluxed for 4 hours, the solvent is evaporated, and the residue is crystallized by iso-propanol (V=0.5 L) and then, dried to obtain a white crystalline of 2,5-diacetoxybenzoic acid 4-iodophenyl ester (mw=440.2 g/mol, 0.212 mol, m=93.5 gr). The yield of the product is 62%.

Synthesis Example 1e-2: Synthesis of 2,5-dihydroxybenzoic Acid 4-iodophenyl Ester Reaction Scheme 1e-2

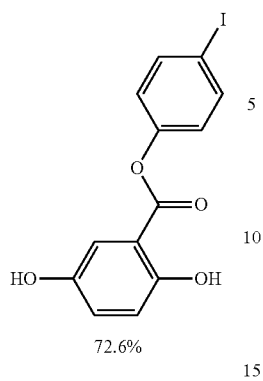

72.6%

2,5-diacetoxybenzoic acid 4-iodophenyl ester (mw=440.2 g/mol, 0.199 mol, m=87.5 gr) is dissolved in a mixture of methanol (V=0.1 L) and DCM (V=0.9 L) to obtain a solution, and para-toluenesulfonic acid monohydrate (mw=190.2 g/mol, 0.417 mol, m=79.4 gr) is added thereto to the solution. The resulting mixture is stirred for 24 hours at 25° C. under a nitrogen atmosphere. The solvent is evaporated under a reduced pressure, and 1 L of water is added to a brown residue to obtain a light pink solid. The solid is filtered, washed with water, and dried under a reduced pressure at 100° C. for 24 hours to obtain an off-white product. The yield of the product is 72.6%.

Synthesis Example 1e-3: Synthesis of 2,5-dihydroxybenzoic Acid 4-(4-phenylethynyl-phenylethynyl)phenyl Ester Reaction Scheme 1e-3

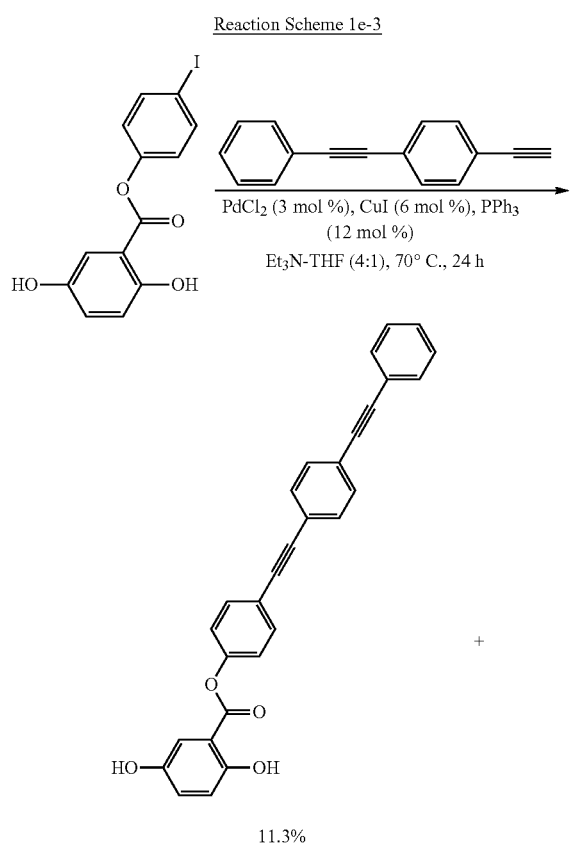

11.3%

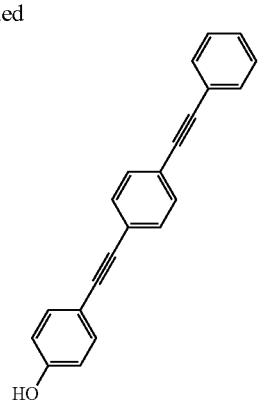

2,5-dihydroxybenzoic acid 4-iodophenyl ester (mw=356.12 g/mol, 0.144 mol, m=51.2 gr) and 1-ethynyl-4-phenylethynylbenzene (mw=202.26 g/mol, 0.158 mmol, m=32 gr) are dissolved in a mixture of 0.8 L of $Et_3N$ and 0.3 L of THF in a 1 L two-necked round bottom flask equipped with a nitrogen inlet and a condenser. The resulting solution is purged with a dry nitrogen gas for 1 hour. Palladium (II) chloride (mw=177.33 g/mol, 4.3 mmol, m=0.76 gr), copper (I) iodide (mw=190.45 g/mol, 8.6 mmol, m=1.64 gr), and triphenylphosphine (mw=262.45 g/mol, 17.2 mmol, m=4.5 gr) are added to the solution. A nitrogen flow is kept for additional 10 minutes, then, a nitrogen outlet is closed, and the mixture is kept stirred under nitrogen at 70° C. for 24 hours. After the reaction is complete, the solvent is evaporated under a reduced pressure to obtain a residue, and the residue is suspended in 1 L of water, filtered, and dried. The obtained yellow solid is treated with 1 L of ethyl acetate and filtered. The solvent is evaporated under a reduced pressure to obtain 2,5-dihydroxybenzoic acid 4-(4-phenylethynyl-phenylethynyl)phenyl ester (a minor product) and 4-(4-phenylethynylphenylethynyl)phenol (a major product). The mixture is suspended in 500 mL of boiling methanol and filtered. The solid product is recovered and treated with 500 mL of hot methanol three times to obtain 2,5-dihydroxybenzoic acid 4-(4-phenylethynylphenylethynyl)phenyl ester. The yield of the product is 11.3%.

Synthesis Example 1e-4: Synthesis of 2,5-bis-[4-(6-acryloyloxyhexyloxy)benzoyloxy]benzoic Acid 4-(4-phenylethynyl-phenylethynyl)benzyl Ester After the reaction is complete, the dark-brown solution is poured into 1 L of water and stirred for 1 hour. After filtering solids, the solids are washed with water (V=500 mL) and methanol (V=200 mL), and recrystallized with a mixture of

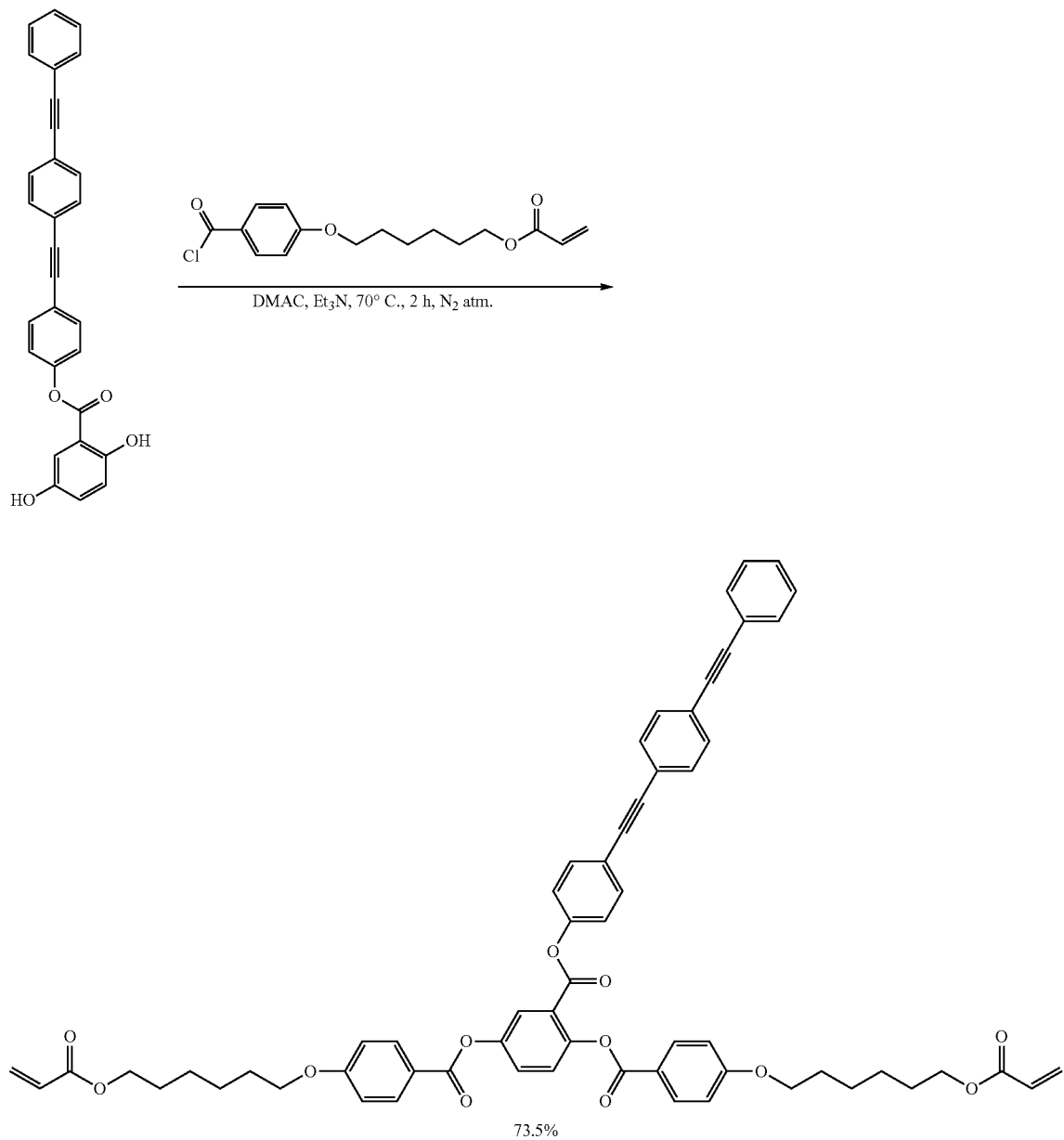

Reaction Scheme 1e-4

73.5%

2,5-dihydroxybenzoic acid 4-(4-phenylethynyl-phenyl-ethynyl)phenyl ester (mw=430.46 g/mol, 15.33 mmol, m=6.6 gr) is dissolved in 100 mL of dimethyl acetamide (DMAC) to obtain a first solution, and a second solution of acrylic acid 6-(4-chlorocarbonylphenoxy)hexyl ester (mw=310.78 g/mol, 46.11 mmol, m=14.33 gr) dissolved in 100 mL of DMAC is added to the first solution while stirring the resultant. Then, triethylamine (mw=101 g/mol, 77 mmol, m=7.8 gr) is added thereto, and the resulting mixture is stirred under a nitrogen gas atmosphere at 70° C. for 2 hours.

charcoal and methanol-dichloromethane twice. The solids are dried at 60° C. for 24 hours under a reduced pressure to obtain a brown solid (mw=979.1 g/mol, 11.26 mmol, m=10.2 gr). The yield of the product is 73.5%.

Comparative Synthesis Example 1: Liquid Crystal Compound of Chemical Formula 1f

A liquid crystal compound represented by Chemical Formula 1f is synthesized according to the following process.

Chemical Formula 1f
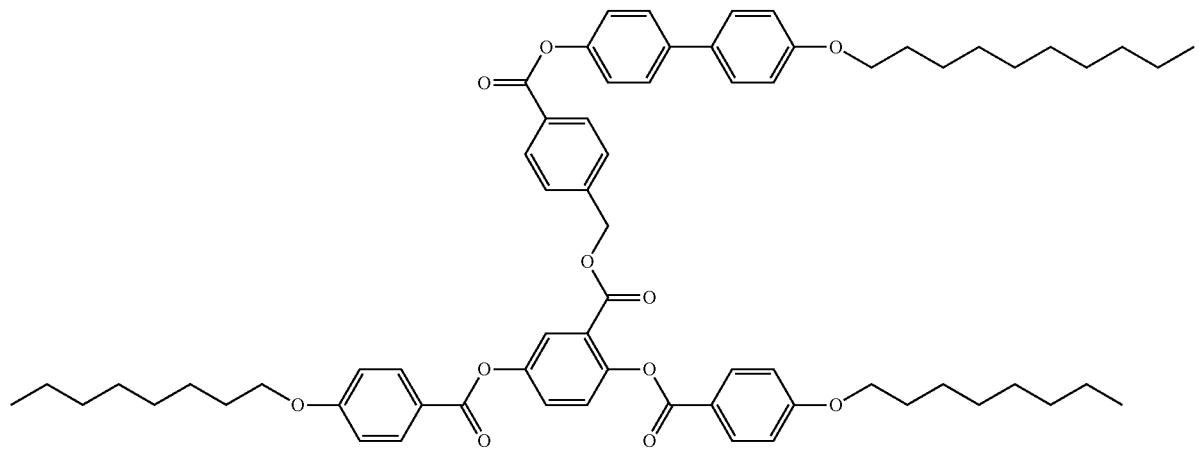
Comparative Synthesis Example 1f-1: Synthesis of
4-chloromethyl-benzoic Acid
4'-decyloxybiphenyl-4-yl Ester
Reaction Scheme 1f-1
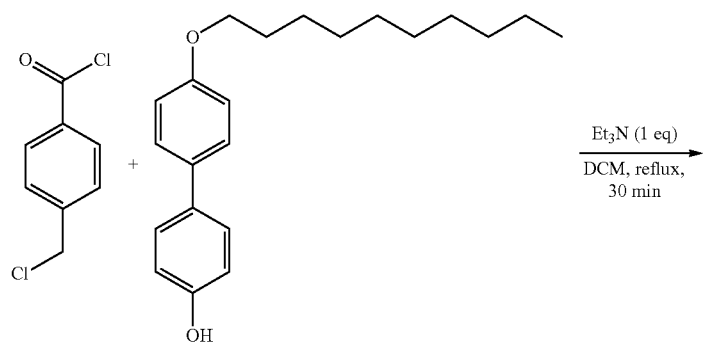
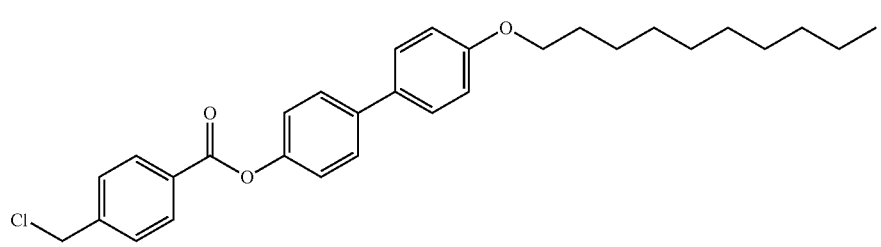

4'-decylbiphenyl-4-ol (10 mmol, 1 equivalent (eq.)) is dissolved in 100 mL of freshly distilled DCM, and triethylamine (11 mmol, 1.1 eq.) is added to the obtained solution. 4-chloromethylbenzoyl chloride (10.5 mmol, 1.05 eq.) is added while stirred, and the mixture is stirred and refluxed under a nitrogen gas atmosphere for 30 minutes.

After completing the reaction and cooling the resultant to room temperature, 150 mL of iso-propanol is added to the mixture, and DCM is distilled off under a reduced pressure. The resulting solid material is filtered and washed with iso-propanol (3×50 mL) and n-hexane (3×50 mL). The material is dried under a reduced pressure at 60° C. for 24 hours to obtain 4-chloromethyl-benzoic acid 4'-decyloxybiphenyl-4-yl ester as a white crystalline solid. The yield of the product is 96%.

Comparative Synthesis Example 1f-2: Synthesis of 2,5-dihydroxy-benzoic Acid 4-(4'-decyloxybiphenyl-4-yloxycarbonyl)-benzyl Ester

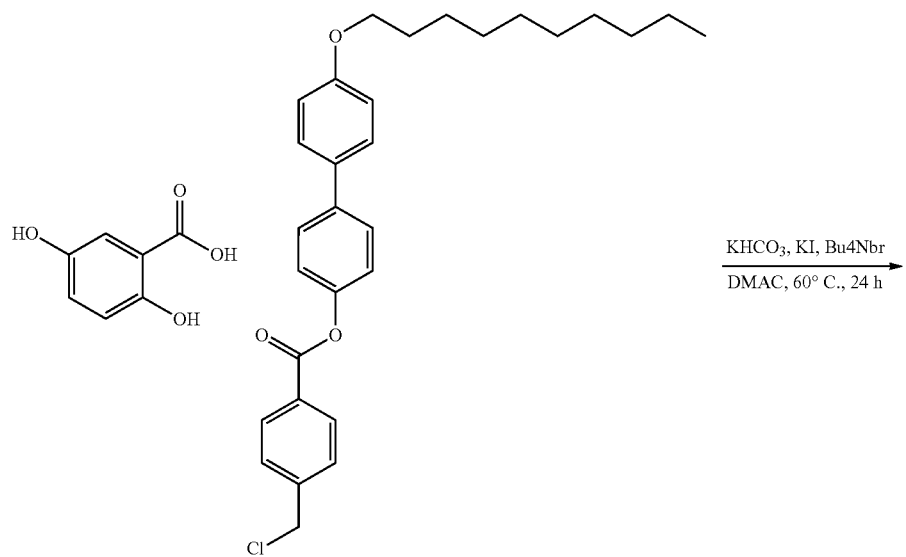

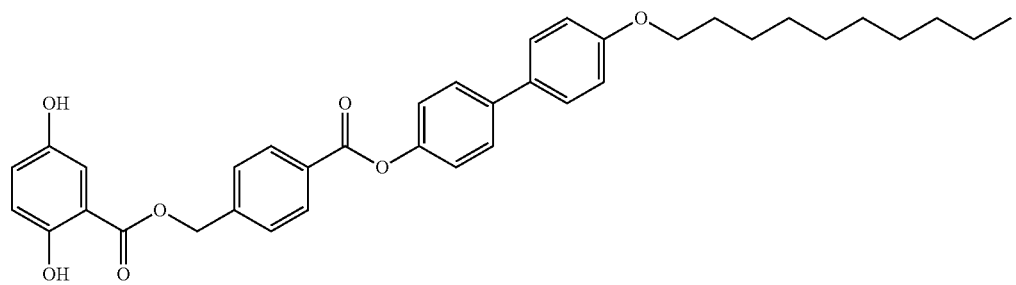

4-chloromethyl-benzoic acid 4'-decyloxybiphenyl-4-yl ester (10 mmol, 1 eq.) of Comparative Synthesis Example 1f-1, 2,5-dihydroxybenzoic acid (10.5 mmol, 1.05 eq.), potassium hydrogen carbonate (KHCO$_3$, 20 mmol, 2 eq.), potassium iodide (KI, 1 mmol, 0.1 eq.), tetra-n-butylammonium bromide (n-Bu$_4$NBr, 0.5 mmol, 0.05 eq.), and distilled dimethyl acetamide (DMAC, 20 mL) are stirred under a nitrogen atmosphere at 60° C. for 24 hours. After the reaction is complete, the mixture is cooled to room temperature and poured into 200 mL of water. The resulting solid is filtered and washed with water (3×100 mL). The solid is air-dried twice and crystallized with DCM/EtOH including a small amount of charcoal. The resulting material is dried under reduced pressure at 60° C. for 24 hours. A greenish powder is obtained using TLC silica gel (eluent: ethyl acetate:hexane=1:4 volume ratio). The yield is 88%.

Comparative Synthesis Example 1f-3: Synthesis of 2,5-bis-(4-octyloxybenzoyloxy)-benzoic Acid 4-(4'-decyloxybiphenyl-4-yloxycarbonyl)-benzyl Ester Reaction Scheme 1f-3

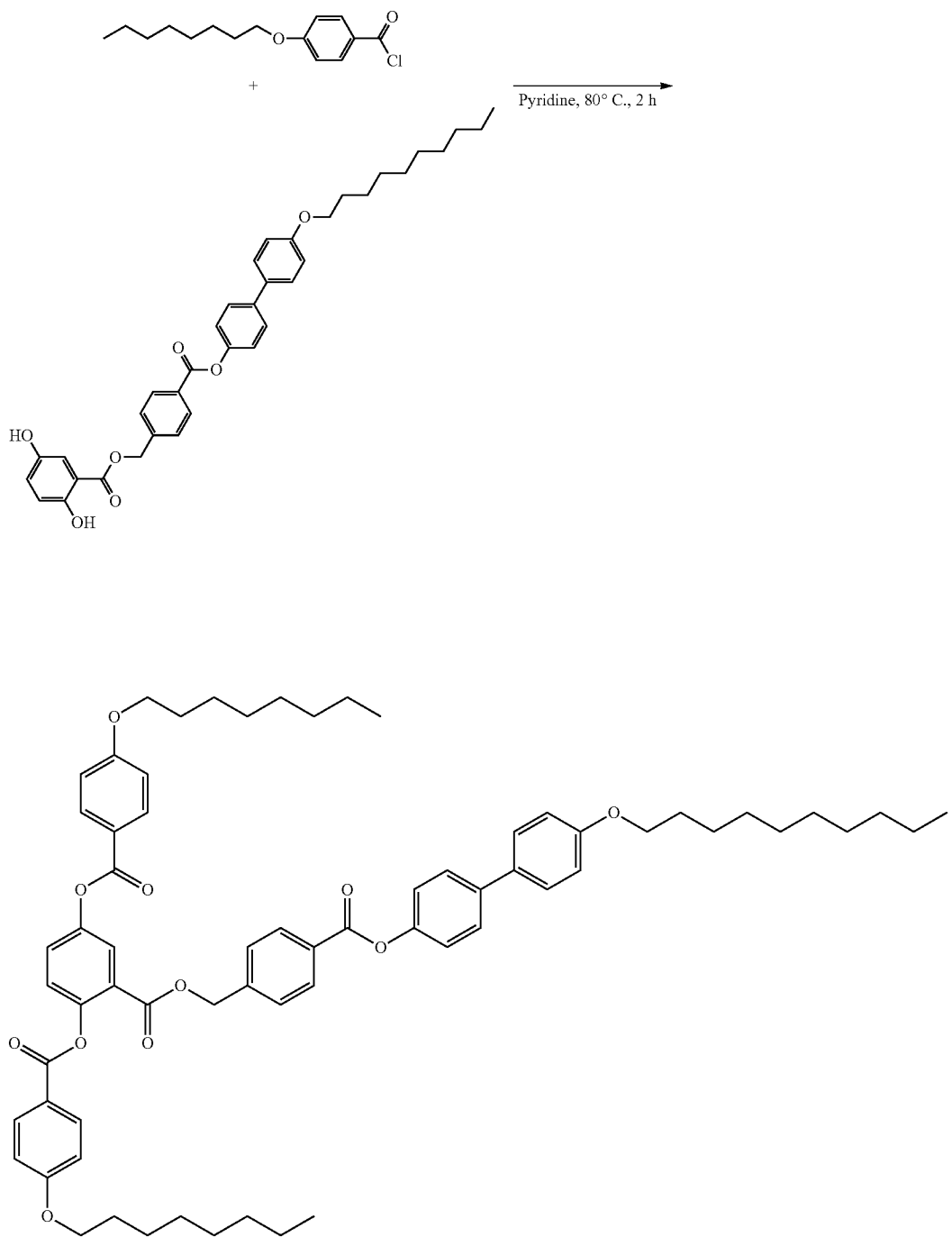

A mixture of 2,5-dihydroxy-benzoic acid 4-(4'-decyloxy-biphenyl-4-yl oxycarbonyl)-benzyl ester (10 mmol, 1 eq.) of Comparative Synthesis Example 1f-2 and 4-octyloxybenzoyl chloride (22 mmol, 2.2 eq.) is stirred in 100 mL of pyridine at 80° C. for 2 hours under a nitrogen atmosphere. After the reaction is complete, the mixture is poured in to 500 mL of water to generate a precipitate. The precipitate is filtered, washed with water, and crystallized with acetone. The resulting material is dried under a reduced pressure at 60° C. for 24 hours to obtain a white solid. 2,5-bis-(4-octyloxybenzoyloxy)-benzoic acid 4-(4'-decyloxybiphenyl-4-yloxycarbonyl)-benzyl ester is obtained using a TLC silica gel (eluent:ethyl acetate:hexane=1:4 volume ratio). The yield is 70%.

Thermal Stability of Liquid Crystal Compound

A thermogravimetric analysis (TGA) is performed with the polymerizable liquid crystal compounds according to Synthesis Examples 1 to 5 by using Universal V4.5A (TA Instruments, 10 degrees Centigrade per minute (° C./min), $N_2$ atmosphere). The analysis results of the polymerizable liquid crystal compounds according to Synthesis Examples 1, 3, 4, and 5 are respectively shown in FIGS. 8, 9, 10, and 11.

Figure 8:
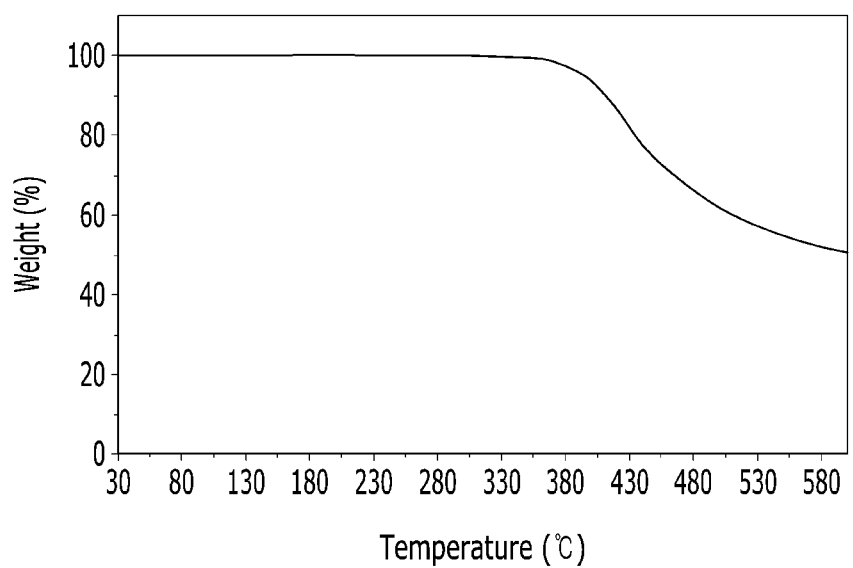
FIG. 8 is a graph of weight (percent, %) versus temperature (degrees Centigrade, ° C.) showing results of a thermogravimetric analysis of the polymerizable liquid crystal compound according to Synthesis Example 1 (the compound of Chemical Formula 1a)
Figure 9:
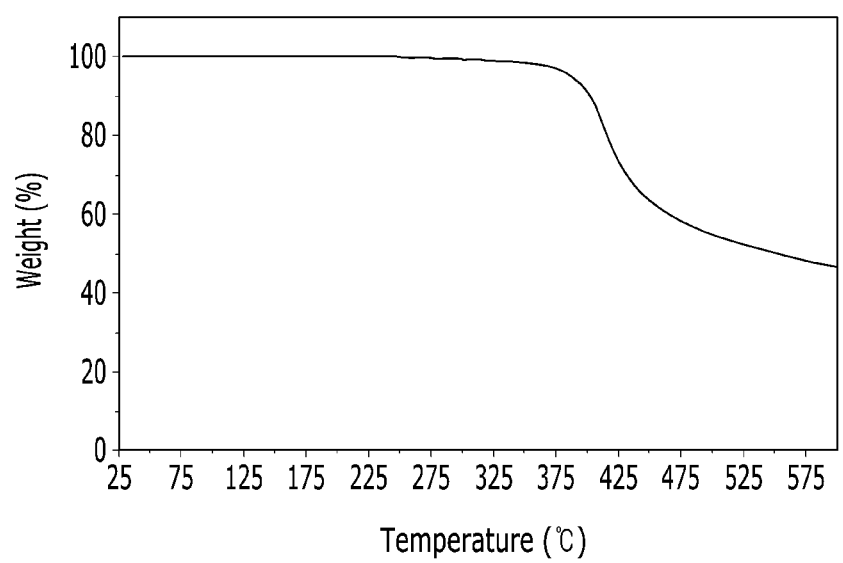
FIG. 9 is a graph of weight (percent, %) versus temperature (degrees Centigrade, ° C.) showing results of a thermogravimetric analysis of the polymerizable liquid crystal compound according to Synthesis Example 3 (the compound of Chemical Formula 1c)
Figure 10:
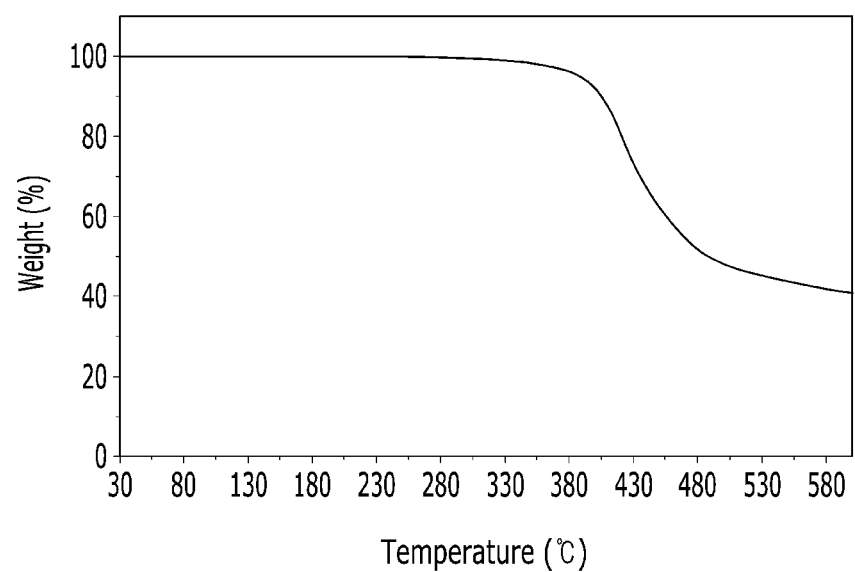
FIG. 10 is a graph of weight (percent, %) versus temperature (degrees Centigrade, ° C.) showing results of a thermogravimetric analysis of the polymerizable liquid crystal compound according to Synthesis Example 4 (the compound of Chemical Formula 1d)
Figure 11:
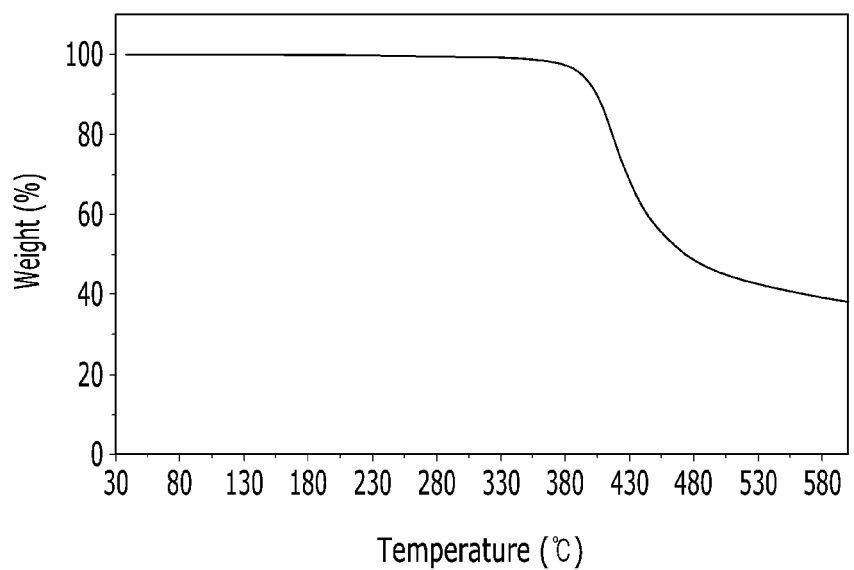
FIG. 11 is a graph of weight (percent, %) versus temperature (degrees Centigrade, ° C.) showing results of a thermogravimetric analysis of the polymerizable liquid crystal compound according to Synthesis Example 5 (the compound of Chemical Formula 1e)

FIG. 8 is a graph showing a thermogravimetric analysis of the polymerizable liquid crystal compound according to Synthesis Example 1 (the compound of Chemical Formula 1a), FIG. 9 is a graph showing a thermogravimetric analysis of the polymerizable liquid crystal compound according to Synthesis Example 3 (the compound of Chemical Formula 1c), FIG. 10 is a graph showing a thermogravimetric analysis of the polymerizable liquid crystal compound according to Synthesis Example 4 (the compound of Chemical Formula 1d), and FIG. 11 is a graph showing a thermogravimetric analysis of the polymerizable liquid crystal compound according to Synthesis Example 5 (the compound of Chemical Formula 1e).

Referring to FIG. 8, the polymerizable liquid crystal compound (Chemical Formula 1a) according to Synthesis Example 1 loses 0.1 wt % at a temperature of 308° C. and 1 wt % at a temperature of 360° C. Referring to FIG. 9, the polymerizable liquid crystal compound (Chemical Formula 1c) according to Synthesis Example 3 loses 1 wt % at a temperature of 330.1° C. Referring to FIG. 10, the polymerizable liquid crystal compound (Chemical Formula 1d) according to Synthesis Example 4 loses 1 wt % at a temperature of 330° C. Referring to FIG. 11, the polymerizable liquid crystal compound (Chemical Formula 1e) according to Synthesis Example 5 loses 1 wt % at a temperature of 346° C. Accordingly, the compounds according to Synthesis Examples 1, 3, 4, and 5 show excellent polymerizable liquid crystal thermal stability.

Stability of Liquid Crystal Compound in Liquid Crystal Phase

Figure 12:
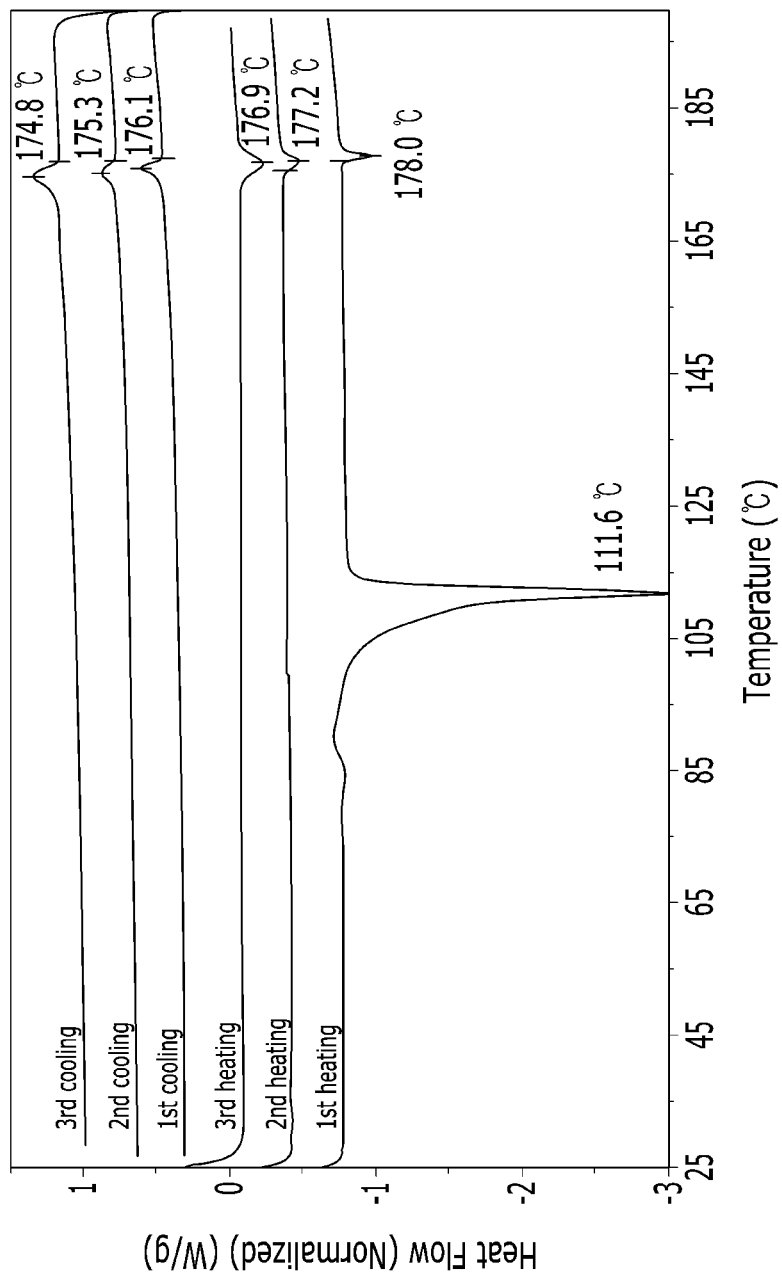
FIG. 12 is a graph of normalized heat flow (watts per gram) versus temperature (degrees Centigrade, ° C.) showing a differential scanning calorimetry analysis results of the polymerizable liquid crystal compound according to Synthesis Example 1.

A differential scanning calorimetry (DSC) analysis is performed with the polymerizable liquid crystal compound according to Synthesis Examples 1 to 5 and the liquid crystal compound according to Comparative Synthesis Example 1 by using Tros V3.2 (TA Instruments, 10° C./min, $N_2$ atmosphere). The analysis results of the polymerizable liquid crystal compound according to Synthesis Example 1 and the compound according to Comparative Synthesis Example 1 are respectively shown in FIGS. 12 and 13. FIG. 12 is a graph showing a differential scanning calorimetry analysis result of the polymerizable liquid crystal compound according to Synthesis Example 1, and FIG. 13 is a graph showing a differential scanning calorimetry analysis result of the liquid crystal compound according to Comparative Synthesis Example 1.

Referring to FIG. 12, in a first heating cycle, a phase transition from a crystalline phase to a nematic phase occurs at a temperature of 111.6° C., and another phase transition from the nematic phase to an isotropic phase occurs at a temperature of 178.0° C. In other words, the polymerizable liquid crystal compound according to Synthesis Example 1 is present in the nematic phase from 111.6° C. to 178.0° C. during a section of about 66.4° C. Referring to FIG. 12, in a second heating cycle, a phase transition from a crystalline phase to a nematic phase occurs at a temperature of 104.3° C., and another phase transition from the nematic phase to an isotropic phase occurs at a temperature of 177.2° C. In other words, the polymerizable liquid crystal compound according to Synthesis Example 1 is present in the nematic phase from 104.3° C. to 177.2° C. during a section of about 72.9° C. In this way, as a compound is present in the nematic phase during a larger temperature section, an optical film having excellent optical properties may be provided.

Figure 13:
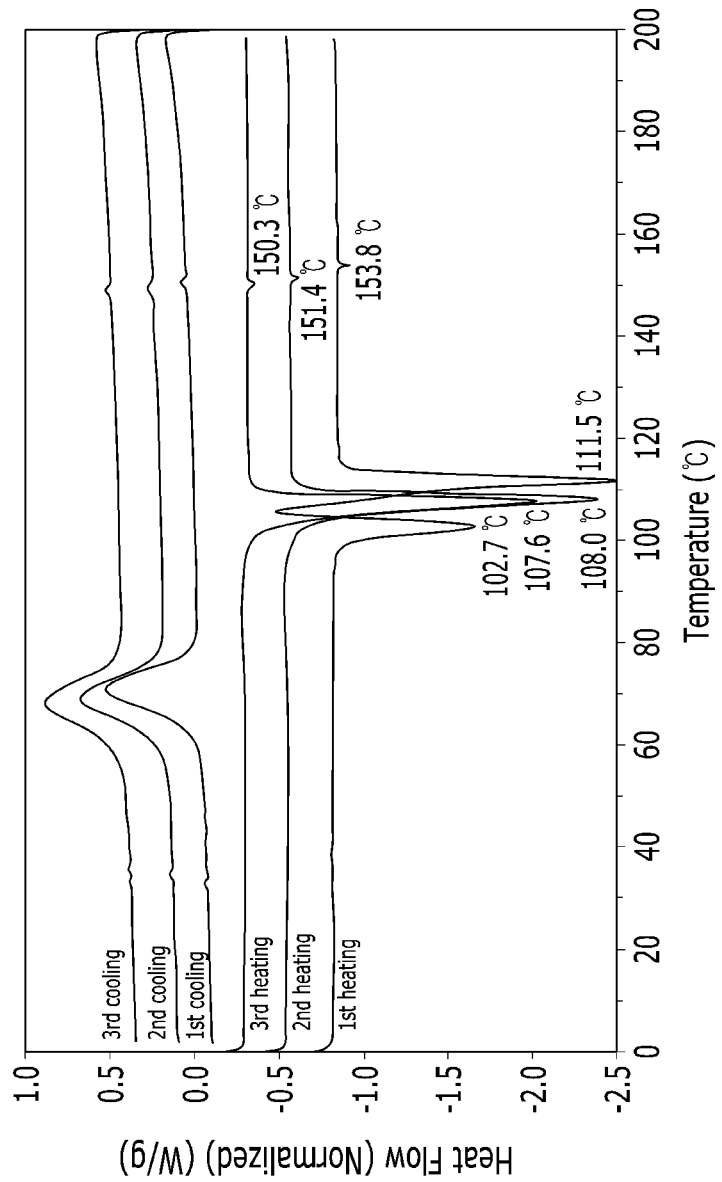
FIG. 13 is a graph of normalized heat flow (watts per gram) versus temperature (degrees Centigrade, ° C.) showing a differential scanning calorimetry analysis results of the liquid crystal compound according to Comparative Synthesis Example 1.

Referring to FIG. 13, in the first heating cycle, the phase transition from a crystalline phase to a nematic phase shows two temperature peaks at 102.7° C. and 111.5° C., and the phase transition from the nematic phase to an isotropic phase occurs at a temperature of 153.8° C. In other words, the liquid crystal compound according to Comparative Synthesis Example 1 is present in the nematic phase from 111.5° C. to 153.8° C. during a section of about 42.3° C.

Referring to FIGS. 12 and 13, the polymerizable liquid crystal compound according to Synthesis Example 1 shows excellent stability in a liquid crystal phase compared with the liquid crystal compound according to Comparative Synthesis Example 1.

Birefringence (Δn) of Liquid Crystal Compound

A birefringence Δn (ne−no, ne=a refractive index for extraordinary light, no=a refractive index for ordinary light) of the polymerizable liquid crystal compounds according to Synthesis Example 1 and the liquid crystal compound represented by the following Chemical Formula 1g (BASF) at a wavelength of 450 nm, 550 nm, and 650 nm is measured, and the results are provided in Table 1.

Chemical Formula 1g

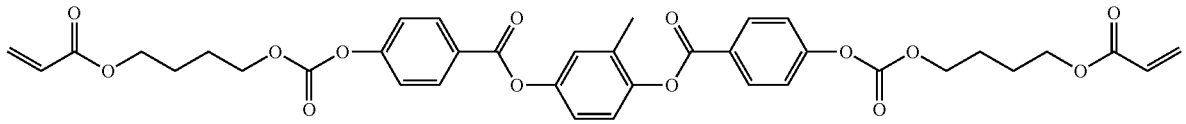

TABLE 1

| | Δn | | |
|---|---|---|---|
| | 450 nm | 550 nm | 650 nm |
| Synthesis Example 1 | 0.073 | 0.081 | 0.082 |
| Chemical Formula 1g | 0.179 | 0.165 | 0.159 |

Referring to Table 1, the compound according to Synthesis Example 1 satisfies $0.05 \leq \Delta n \leq 0.1$ at each wavelength, and the compound represented by Chemical Formula 1g has Δn of larger than 0.1.

Example 1: Manufacture of Optical Film

The polymerizable liquid crystal compound according to Synthesis Example 1 and the liquid crystal compound (BASF) represented by Chemical Formula 1g are mixed in a weight ratio of 75:25, 16 wt % of the mixture, 3 wt % of a photoinitiator (Irgacure907, CIBA Specialty Chemicals Inc.), 1 wt % of a sensitizer (DETX, Sigma-Aldrich Co., Ltd.), and 80 wt % of a mixed solvent of toluene and cyclohexanone (7:3 weight to weight, wt/wt) are mixed, and the obtained mixture is stirred on a 45° C. hot plate for 1 hour to prepare a composition for an optical film.

The composition for an optical film is spin-coated on a 1 millimeter thick (mm-thick) glass substrate at 1,000 revolutions per minute (rpm) for 30 seconds. Subsequently, the substrate is dried in an 80° C. oven for 2 minutes and is allowed to stand at room temperature for 2 minutes, cooled, and radiated by ultraviolet (UV) with a light dose of 1000 millijoules per square centimeter (mJ/cm$^2$) to manufacture an optical film including a liquid crystal layer cured on the substrate.

Examples 2 to 5: Manufacture of Optical Film

An optical film is manufactured according to the same method as Example 1 by respectively using the polymerizable liquid crystal compound according to Synthesis Examples 2 to 5 instead of the polymerizable liquid crystal compound according to Synthesis Example 1.

Example 6 to 11: Manufacture of Optical Film

The polymerizable liquid crystal compound according to Synthesis Example 1 and the liquid crystal compound (BASF) represented by Chemical Formula 1g are mixed in each weight ratio of 5:95, 10:90, 30:70, 50:50, 70:30, and 100:0, 16 wt % of the mixture, 3 wt % of a photoinitiator (Irgacure907, CIBA Specialty Chemicals Inc.), 1 wt % of a sensitizer (DETX, Sigma-Aldrich Co., Ltd.), and 80 wt % of a mixed solvent of toluene and cyclohexanone (7:3 wt/wt) are mixed, and the obtained mixture is stirred on a 45° C. hot plate for one hour, preparing a composition for an optical film.

The composition for an optical film is spin-coated on a 1 mm-thick glass substrate at 1,000 rpm for 30 seconds. Subsequently, the substrate is dried in an 80° C. oven for 2 minutes and at room temperature for 2 minutes, cooled down, and radiated by ultraviolet (UV) with a light dose of 1,000 mJ/cm$^2$ on a substrate to manufacture each optical film according to Examples 6 to 11 including a liquid crystal layer cured on the substrate.

Comparative Example 1: Manufacture of Optical Film 16 wt % of the liquid crystal compound according to Comparative Synthesis Example 1, 3 wt % of a photoinitiator (Irgacure907, CIBA Specialty Chemicals Inc.), 1 wt % of a sensitizer (DETX, Sigma-Aldrich Co., Ltd.), and 80 wt % of a mixed solvent of toluene and cyclohexanone (7:3 wt/wt) are mixed, and the obtained mixture is stirred on a 45° C. hot plate for one hour to prepare a composition for an optical film.

The composition for an optical film is spin-coated on a 1 mm-thick glass substrate at 1,000 rpm for 30 seconds. Subsequently, the substrate is dried in an 80° C. oven for 2 minutes and at room temperature for 2 minutes, cooled, and radiated by ultraviolet (UV) with a light dose of 1,000 mJ/cm$^2$ to manufacture an optical film including a liquid crystal layer cured on the substrate.

In-plane retardation of the optical film is measured by using AxoScan™ (Axometrics). The results are provided in Table 2.

TABLE 2

| Example | $R_e$ (450 nm) | $R_e$ (550 nm) | $R_e$ (650 nm) | $R_e$ (450 nm)/$R_e$ (550 nm) | $R_e$ (650 nm)/$R_e$ (550 nm) |
|---|---|---|---|---|---|
| 6 | 45.745 | 43.48 | 36.638 | 1.05 | 0.84 |
| 7 | 46.425 | 45.138 | 37.014 | 1.03 | 0.82 |
| 8 | 47.49 | 44.035 | 46.365 | 1.08 | 1.05 |
| 9 | 56.207 | 48.373 | 45.997 | 1.16 | 0.95 |
| 10 | 65.79 | 56.21 | 54.43 | 1.17 | 0.97 |
| 11 | 63.296 | 58.108 | 57.551 | 1.09 | 0.99 |

Referring to Table 2, the optical films according to Examples 6 to 11 may realize a flat wavelength dispersion with no almost in-plane retardation change at a wavelength of 450 nm, 550 nm, and 650 nm, and thus reverse wavelength dispersion retardation as well as forward wavelength dispersion retardation.

While this disclosure has been described in connection with what is presently considered to be practical exemplary embodiments, it is to be understood that the disclosure is not limited to the present embodiments, but, on the contrary, is intended to cover various modifications and equivalent arrangements included within the spirit and scope of the appended claims.

What is claimed is:

1. A polymerizable liquid crystal compound represented by Chemical Formula 1:

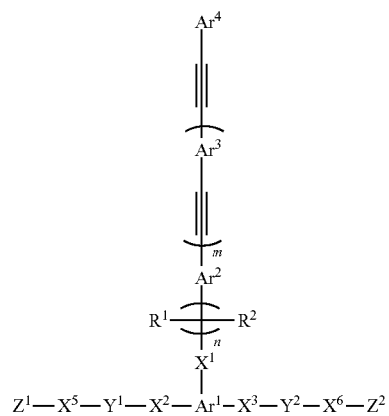

wherein, in Chemical Formula 1,
Ar$^1$ is a substituted or unsubstituted trivalent aromatic hydrocarbon group, Ar² and Ar³ are independently a substituted or unsubstituted divalent aromatic hydrocarbon group,
Ar⁴ is a substituted or unsubstituted monovalent aromatic hydrocarbon group,
X¹ is selected from —C(=O)O— and —C(=O)N(Rᵃ)— (wherein Rᵃ is hydrogen, a C1 to C20 alkyl group, or a C6 to C30 aryl group),
R¹ and R² are independently selected from hydrogen, a halogen, a cyano group, a nitro group, an aldehyde group, a C2 to C30 ketone group, a C2 to C30 ester group, a C1 to C30 alkylsulfonyl group, and a substituted or unsubstituted C1 to C20 alkyl group,
n is an integer of 0 to 2,
m is 1 or 2,
X² and X³ are independently selected from —OC(=O)—, —C(=O)O—, —N(Rᵃ)C(=O)—, and —C(=O)N(Rᵃ)— (wherein Rᵃ is hydrogen, a C1 to C20 alkyl group, or a C6 to C30 aryl group),
Y¹ and Y² are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof,
X⁵ and X⁶ are independently a linking group selected from —OC(=O)—, —C(=O)O—, —S—, —O—, —S(=O)—, —C(=O)—, —S(=O)₂—, —N(Rᵃ)—, —C(=O)S—, —N(Rᵇ)C(=O)—, and —C(=O)N(Rᶜ)— (wherein Rᵃ, Rᵇ, and Rᶜ are independently selected from hydrogen, a C1 to C20 alkyl group, and a C6 to C30 aryl group), or a C2 to C20 alkylene group, wherein at least one —(CH₂)— group is replaced by the above linking group in the main chain, and
Z¹ and Z² are independently a C2 to C30 polymerizable functional group.

2. The polymerizable liquid crystal compound of claim 1, wherein the polymerizable liquid crystal compound represented by Chemical Formula 1 is represented by Chemical Formula 2:

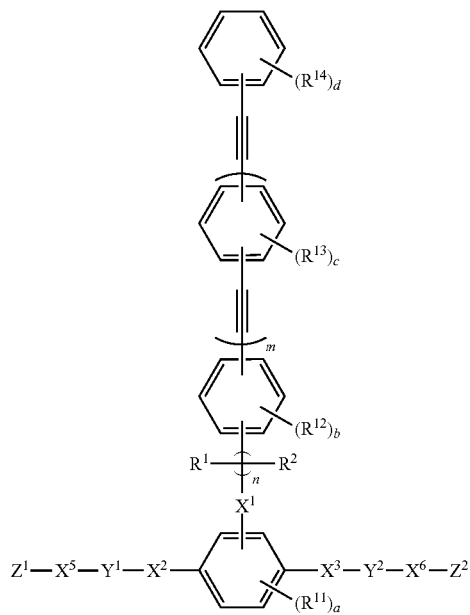

wherein, in Chemical Formula 2,
X¹ is selected from —C(=O)O— and —C(=O)N(Rᵃ)— (wherein Rᵃ is hydrogen, a C1 to C20 alkyl group, or a C6 to C30 aryl group),
R¹ and R² are independently selected from hydrogen, a halogen, a cyano group, a nitro group, an aldehyde group, a C2 to C30 ketone group, a C2 to C30 ester group, a C1 to C30 alkylsulfonyl group, and a substituted or unsubstituted C1 to C20 alkyl group,
n is an integer of 0 to 2,
m is 1 or 2,
R¹¹, R¹², R¹³, and R¹⁴ are independently selected from hydrogen, a halogen, a cyano group, a nitro group, an aldehyde group, and a substituted or unsubstituted C1 to C20 alkyl group,
a, b, c, and d are independently determined according to the valence of phenylene,
X² and X³ are independently selected from —OC(=O)—, —C(=O)O—, —N(Rᵃ)C(=O)—, and —C(=O)N(Rᵃ)— (wherein Rᵃ is hydrogen, a C1 to C20 alkyl group, or a C6 to C30 aryl group),
Y¹ and Y² are independently selected from a substituted or unsubstituted divalent aliphatic hydrocarbon group, a substituted or unsubstituted divalent aromatic hydrocarbon group, a substituted or unsubstituted divalent alicyclic hydrocarbon group, and a combination thereof,
X⁵ and X⁶ are independently a linking group selected from —OC(=O)—, —C(=O)O—, —S—, —O—, —S(=O)—, —C(=O)—, —S(=O)₂—, —N(Rᵃ)—, —C(=O)S—, —N(Rᵇ)C(=O)—, and —C(=O)N(Rᶜ)— (wherein Rᵃ, Rᵇ, and Rᶜ are independently selected from hydrogen, a C1 to C20 alkyl group, and a C6 to C30 aryl group), or a C2 to C20 alkylene group, wherein at least one —(CH₂)— group is replaced by the above linking group in the main chain, and
Z¹ and Z² are independently a C2 to C30 polymerizable functional group.

3. The polymerizable liquid crystal compound of claim 1, wherein Ar¹ is a functional group represented by Chemical Formula 1-1:

 (1)

 (2)

 (3)

 (4)

-continued (5)

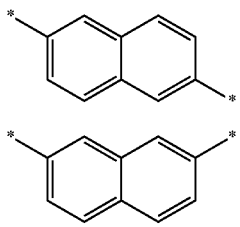

(6)

wherein, in Chemical Formula 1-1,
a hydrogen bound to each aromatic ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)$R^a$), a substituted or unsubstituted C2 to C20 ester group (—C(=O)O$R^b$), a substituted or unsubstituted C3 to C30 cycloalkyl group, a substituted or unsubstituted C6 to C30 aryl group, —S(=O)$R^c$, —S(=O)O$R^d$, —S(=O)$_2R^e$, or —S(=O)$_2$O$R^f$ (wherein $R^a$ to $R^f$ are selected from hydrogen, a C1 to C20 alkyl group, and a C6 to C30 aryl group),
at least one =CH— group of each aromatic ring is optionally replaced by =N—, and
two asterisks indicates linking points bound to $X^2$ and $X^3$.

4. The polymerizable liquid crystal compound of claim 1, wherein in Chemical Formula 1, —C($R^1$)($R^2$)— is a functional group represented by Chemical Formula 1-2:

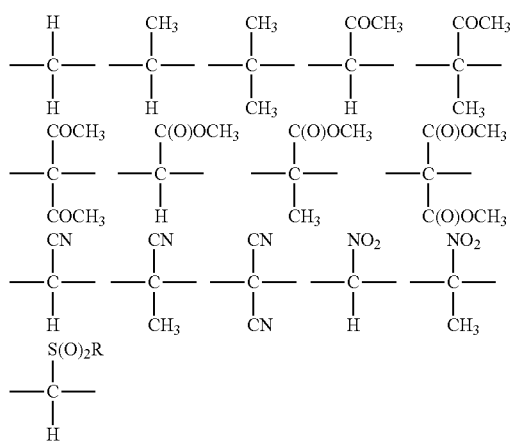

wherein, in Chemical Formula 1-2,
R is selected from a C1 to C20 alkyl group and a C6 to C30 aryl group.

5. The polymerizable liquid crystal compound of claim 1, wherein $Y^1$ and $Y^2$ are independently a functional group represented by Chemical Formula 1-3:

(1)

-continued (2)

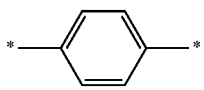

(3)

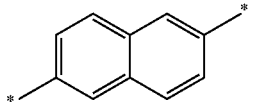

(4)

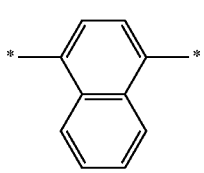

(5)

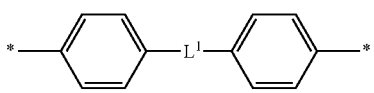

(6)

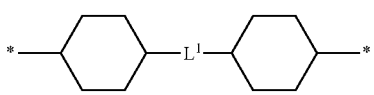

(7)

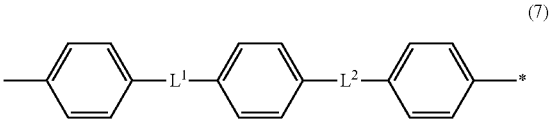

wherein, in Chemical Formula 1-3,
$L^1$ and $L^2$ are independently a single bond or a linking group selected from —C($R^x$)=C($R^y$)— (wherein $R^x$ and $R^y$ are independently hydrogen, a C1 to C20 alkyl group, or a C6 to C30 aryl group), —C≡C—, —O—, —S—, —N($R^a$)—, —C(=O)—, —C(=O)O—, —OC(=O)—, —SC(=O)—, —C(=O)S—, —N($R^b$)C(=O)—, and —C(=O)N($R^c$)— (wherein $R^a$ to $R^c$ is hydrogen, a C1 to C20 alkyl group, or a C6 to C30 aryl group) or a C2 to C20 alkylene group, wherein at least one —(CH$_2$)— group is replaced by the above linking group selected from —C($R^x$)=C($R^y$)—, —C≡C—, —O—, —S—, —N($R^a$)—, —C(=O)—, —C(=O)O—, —OC(=O)—, —OC(=O)—, —C(=O)S—, —N($R^b$)C(=O)—, and —C(=O)N($R^c$)— (wherein Rfx, $R^y$, and $R^a$ to $R^c$ are the same as described above) in the main chain,
a hydrogen bound to each cyclohexylene ring, each phenylene ring, and each naphthylene ring is optionally replaced by a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)$R^a$), a substituted or unsubstituted C2 to C20 ester group (—C(=O)O$R^b$), a substituted or unsubstituted C3 to C30 cycloalkyl group, a substituted or unsubstituted C6 to C30 aryl group, —S(=O)$R^c$, —S(=O)O$R^d$, —S(=O)$_2R^e$, or —S(=O)$_2$O$R^f$ (wherein $R^a$ to $R^f$ are selected from hydrogen, a C1 to C20 alkyl group, and a C6 to C30 aryl group), and
at least one non-adjacent —(CH$_2$)— group of each cyclohexylene ring is optionally replaced by —O—, —S—, or —N($R^a$)— (wherein $R^a$ is selected from hydrogen, a C1 to C20 alkyl group, and a C6 to C30 aryl group), and at least one non-adjacent =CH— group of each phenylene ring or each naphthylene ring is optionally replaced by =N—.

6. The polymerizable liquid crystal compound of claim 1, wherein the polymerizable functional group is selected from a substituted or unsubstituted C2 to C10 alkenyl group, a substituted or unsubstituted C2 to C10 alkynyl group, a substituted or unsubstituted oxetanyl group, a substituted or unsubstituted (meth)acryl group, a substituted or unsubstituted (meth)acryloyloxy group, a substituted or unsubstituted (meth)acryloylamino group, a substituted or unsubstituted (meth)acryloyl group, a substituted or unsubstituted maleoyl group, a substituted or unsubstituted epoxy alkyl group, and a substituted or unsubstituted epoxy cycloalkyl group.

7. The polymerizable liquid crystal compound of claim 1, wherein in Chemical Formula 1, the polymerizable functional group is a functional group represented by Chemical Formula 1-4:

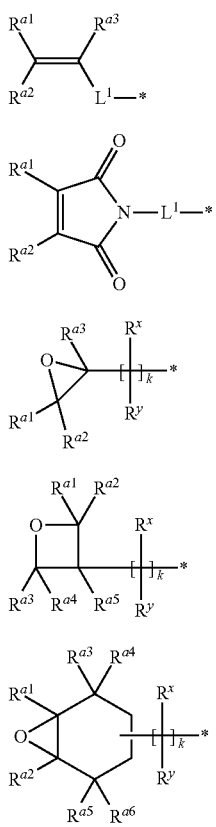

wherein, in Chemical Formula 1-4,
* indicates a site bound to $X^5$ or $X^6$ in Chemical Formula 1,
$R^{a1}$, $R^{a2}$, $R^{a3}$, $R^{a4}$, $R^{a5}$, and $R^{a6}$ are independently selected from hydrogen, a halogen, C1 to C6 alkyl group and C1 to C6 haloalkyl group,
$L^1$ is a single bond or a linking group selected from —O—, —C(=O)—, —OC(=O)—, and —C(=O)O— or a C2 to C20 alkylene group, wherein at least one —(CH$_2$)— group is replaced by the above the linking group in the main chain,
$R_x$ and $R_y$ are independently selected from hydrogen, a halogen, a cyano group, a nitro group, an aldehyde group, an amine group, a carboxylic acid group, a substituted or unsubstituted C1 to C20 alkyl group, a substituted or unsubstituted C2 to C20 alkenyl group, a substituted or unsubstituted C2 to C20 alkynyl group, a substituted or unsubstituted C2 to C20 ketone group (—C(=O)R$^a$), a substituted or unsubstituted C2 to C20 ester group (—C(=O)OR$^b$), a substituted or unsubstituted C3 to C30 cycloalkyl group, a substituted or unsubstituted C6 to C30 aryl group, —S(=O)R$^c$, —S(=O)OR$^d$, —S(=O)$_2$R$^e$, and —S(=O)$_2$OR$^f$ (wherein R$^a$ to R$^f$ are selected from hydrogen, a C1 to C20 alkyl group, and a C6 to C30 aryl group), and
k is an integer of 0 to 10, provided that when k is 2 or more, at least one non-adjacent —(CR$^x$R$^y$)— is optionally replaced by a linking group selected from —O—, —C(=O)—, —OC(=O)—, and —C(=O)O—.

8. The polymerizable liquid crystal compound of claim 1, wherein the polymerizable liquid crystal compound has Δn, which is a difference between a refractive index for extraordinary light and a refractive index for ordinary light, that satisfies Relationship Equation 1:

$$0.05 \le \Delta n \le 0.1$$

wherein in Relationship Equation 1,
Δn=ne−no, wherein ne denotes a refractive index for extraordinary light, and no denotes a refractive index for ordinary light.

9. A composition for an optical film comprising the polymerizable liquid crystal compound of claim 1.

10. The composition for an optical film of claim 9, wherein the composition for an optical film further comprises a rod-shaped liquid crystal compound.

11. The composition for an optical film of claim 10, wherein the composition for an optical film comprises the polymerizable liquid crystal compound and the rod-shaped liquid crystal compound in a weight ratio of about 20:80 to about 80:20.

12. An optical film comprising:
a substrate, and
a liquid crystal layer disposed on one surface of the substrate,
wherein the liquid crystal layer comprises the composition for an optical film of claim 1.

13. The optical film of claim 12, wherein the liquid crystal layer further comprises a rod-shaped liquid crystal compound.

14. The optical film of claim 13, wherein the liquid crystal layer comprises the polymerizable liquid crystal compound and the rod-shaped liquid crystal compound in a weight ratio of about 20:80 to about 80:20.

15. The optical film of claim 13, wherein the liquid crystal layer comprises:
a first liquid crystal layer comprising the polymerizable liquid crystal compound and a rod-shaped liquid crystal compound, and
a second liquid crystal layer comprising a rod-shaped liquid crystal compound.

16. The optical film of claim 12, wherein the optical film has forward wavelength dispersion retardation or reverse wavelength dispersion retardation.

17. A compensation film comprising:
an optical film comprising a substrate and a liquid crystal layer disposed on one surface of the substrate, wherein the liquid crystal layer comprises the polymerizable liquid crystal compound of claim 1, and
a retardation film disposed on at least one surface of the optical film.

18. The compensation film of claim 17, wherein the liquid crystal layer further comprises a rod-shaped liquid crystal compound.

19. The compensation film of claim 18, wherein the liquid crystal layer comprises the polymerizable liquid crystal compound and the rod-shaped liquid crystal compound in a weight ratio of about 20:80 to about 80:20.

20. The compensation film of claim 17, wherein the optical film has a forward wavelength dispersion retardation or a reverse wavelength dispersion retardation.

21. The compensation film of claim 18, wherein the liquid crystal layer comprises:
 a first liquid crystal layer comprising the polymerizable liquid crystal compound and a rod-shaped liquid crystal compound, and
 a second liquid crystal layer comprising a rod-shaped liquid crystal compound.

22. The compensation film of claim 17, wherein the retardation film is a $\Delta/4$ retardation film, a $\Delta/2$ retardation film, or a combination thereof.

23. An antireflective film comprising:
 the compensation film of claim 17, and
 a polarization film disposed on one surface of the compensation film.

24. A display device comprising:
 a display panel, and
 the optical film of claim 12.

25. A display device comprising:
 a display panel, and
 the compensation film of claim 17.

26. A display device comprising:
 a display panel, and
 the antireflective film of claim 23.

* * * * *